United States Patent [19]
Koizumi et al.

[11] Patent Number: 5,519,051
[45] Date of Patent: May 21, 1996

[54] OXA- OR AZASTEROID DERIVATIVES

[75] Inventors: Naoyuki Koizumi, Sagamihara; Shigehiro Takegawa, Kawasaki; Shigeki Iwashita, Sagamihara; Tomoko Kawachi, Inagi; Teruaki Matsui, Kawasaki; Seijiro Honma, Yokohama; Hiroo Takahashi, Sagamihara; Mamoru Mieda, Ebina; Koichi Minato, Koganei; Kenyu Shibata, Inagi; Mitsuteru Numazawa, Sendai, all of Japan

[73] Assignee: Teikoku Hormone Mfg. Co., Ltd., Tokyo, Japan

[21] Appl. No.: 119,235

[22] PCT Filed: Mar. 26, 1992

[86] PCT No.: PCT/JP92/00364

§ 371 Date: Sep. 28, 1993

§ 102(e) Date: Sep. 28, 1993

[87] PCT Pub. No.: WO92/17489

PCT Pub. Date: Oct. 15, 1992

[30] Foreign Application Priority Data

Mar. 28, 1991 [JP] Japan .................................. 3-087336
Oct. 22, 1991 [JP] Japan .................................. 3-301224

[51] Int. Cl.$^6$ .................... C07D 311/78; A61K 31/35
[52] U.S. Cl. ........................................... 514/453; 549/384
[58] Field of Search ........................... 514/453; 549/384

[56] References Cited

U.S. PATENT DOCUMENTS

| | | | |
|---|---|---|---|
| 3,642,800 | 2/1972 | Nelson et al. | 260/286 R |
| 4,235,893 | 11/1980 | Brodie et al. | 424/243 |
| 4,591,585 | 5/1986 | Kerb et al. | 514/177 |
| 4,596,797 | 6/1986 | Schweikert et al. | 514/177 |
| 4,757,061 | 7/1988 | Faustini et al. | 514/177 |
| 4,808,616 | 2/1989 | Buzzetti et al. | 514/177 |
| 5,227,375 | 7/1993 | Labrie et al. | 514/172 |

FOREIGN PATENT DOCUMENTS

| | | |
|---|---|---|
| 60-13796 | 1/1985 | Japan . |
| 61-189295 | 8/1986 | Japan . |
| 62-12797 | 1/1987 | Japan . |
| WO91/12206 | 8/1991 | WIPO . |

OTHER PUBLICATIONS

CA 114 62401
CA 108 183872
CA 106 102579

The Merck Index, 10th Edition, Entry 8999.
Sherwin et al., J. Med. Chem., "Effects of Steroid D–Ring Modification on Suicide Inactivation and Competitive Inhibition of Aromatase by Analogues of Androsta-1, 4–diene-3, 17–dione", vol. 32, pp. 651–658 (1989).
Kierstead et al., J. Med. Chem. "16–Aza Steroids", vol. 10, pp. 177–181 (1967).
Regan et al., J. Am. Chem. Soc., "17— and 17a–Aza–D–homosteroids", vol. 78, pp. 639–643 (1956).
Suginome et al., J. Org. Chem., "Photoinduced Transformations. 73.$^1$ Transformations of Five— (and Six—) Membered Cyclic Alcohols into Five— (and Six—) Membered Cyclic Ethers–A New Method of a Two-Step Transformation of Hydroxy Steroids into Oxasteroids$^2$", vol. 49, pp. 3753–3762 (1984).
Ryan, The Journal of Biological Chemistry, "Biological Aromatization of Steroids", vol. 234, pp. 268–272 (1959).
Thompson et al., The Journal of Biological Chemistry, "The Involvement of Human Placental Microsomal Cytochrome P–450 in Aromatization", vol. 249, pp. 5373–5378 (1974).

*Primary Examiner*—Gary Geist
*Assistant Examiner*—Catherine Kilby Scalzo
*Attorney, Agent, or Firm*—Wenderoth, Lind & Ponack

[57] ABSTRACT

Compounds are described having the formula wherein

A denotes C=O, $CH_2$, C=$CH_2$ or C=CH-lower alkyl;

B denotes O, NH or N-lower alkyl;

X does not exist, or denotes C=O or $CH_2$;

n denotes 2 or 3 when X does not exist, or denotes 1 or 2 when X denotes C=O or $CH_2$; and the broken line between the 1- and 2-positions of the steroid skeleton means that a double bond may optionally exist there. These compounds have an aromatase inhibition action and are useful for prophylaxis or treatment of diseases caused by excess of estrogens, for example, breast cancer, uterine cancer, prostatic hypertrophy, etc.

5 Claims, No Drawings

OXA- OR AZASTEROID DERIVATIVES

This application is a 371 of PCT/JP 92/00364 filed Mar. 26, 1992.

TECHNICAL FIELD

This invention relates to novel oxa- or azasteroid derivatives having an aromatase inhibition action, and relates in more detail to steroid derivatives represented by the formula

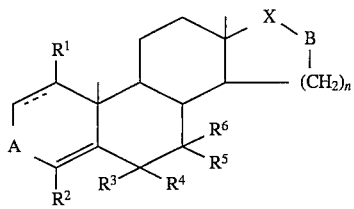

(I)

wherein $R^1$ denotes a hydrogen atom or a lower alkyl group;

$R^2$ denotes a hydrogen atom, a halogen atom, or a hydroxyl, mercapto or amino group which may optionally be acylated or lower alkylated;

$R^3$, $R^4$, $R^5$ and $R^6$ denote one of the following (a) to (d):

(a) $R^3$ and $R^5$ each denote a hydrogen atom, and $R^4$ and $R^6$ each denote a hydrogen atom, a halogen atom or a lower alkyl group, (b) $R^3$ and $R^6$ each denote a hydrogen atom, and $R^4$ and $R^5$ combine to denote a single bond, a methylene group or a dihalomethylene group, (c) $R^3$ and $R^4$ combine to denote an oxo group or a methylene group, and $R^5$ and $R^6$ each denote a hydrogen atom, (d) $R^3$ denotes an acyloxy group, $R^4$ and $R^5$ combine to denote a single bond, and $R^6$ denotes a hydrogen atom;

A denotes C=O, $CH_2$, C=$CH_2$ or C=CH-lower alkyl;

B denotes O, NH or N-lower alkyl;

X does not exist, or denotes C=O or $CH_2$;

n denotes 2 or 3 when X does not exist, or denotes 1 or 2 when X denotes C=O or $CH_2$; and the broken line between the 1- and 2-positions of the steroid skeleton means that a double bond may optionally exist there, provided that the cases of the following (i) to (v) are excluded:

(i) the case where each of $R^1$ to $R^6$ is a hydrogen atom, A is C=O, B is O, X is C=O, n is 1, and a double bond exists between the 1- and 2-positions of the steroid skeleton, (ii) the case where each of $R^1$ to $R^6$ is a hydrogen atom, A is C=O, B is O or NH, X is C=O, n is 1, and the 1- and 2-positions of the steroid skeleton are combined by a single bond, (iii) the case where each of $R^1$, $R^2$, $R^3$ and $R^6$ is a hydrogen atom, $R^4$ and $R^5$ combine to denote a single bond, A is C=O, B is NH, X is C=O, n is 2, and the 1- and 2-positions of the steroid skeleton are combined by a single bond, (iv) the case where B is NH or N-lower alkyl, and X does not exist, and (v) the case where B is NH or N-lower alkyl, X is $CH_2$, A is C=O, C=$CH_2$ or C=CH-lower alkyl.

BACKGROUND ART

Biosynthesis of estrogens occurs when androgens are oxidized with an enzyme called aromatase, formic acid is eliminated, and the androgens are aromatized. Therefore, if it is possible to inhibit the action of aromatase effectively, it is considered to be useful for treatment of diseases caused by excess of estrogens, and, based thereon, it is already revealed that several aromatase inhibitors are useful for treatment of breast cancer and prostatic hypertrophy.

Further, aromatase inhibitors are also useful for treatment of other diseases caused by excess of estrogens, for example, uterine cancer, ovarian cancer, endometriosis, gynecomastia, male infertility based on oligospermia, etc.

As steroidal aromatase inhibitors, there have, for example, been known testolactone (The Merck Index, 10th edition, 8999), 4-hydroxy-4-androstene-3,17-dione and its esters (U.S. Pat. No. 4,235,893), 1-alkylandrosta-1,4-diene-3,17-dione (Japanese Laid-Open Patent Publication No. 13796/1985), 4-substituted androstene-3,17-dione derivatives (Japanese Laid-Open Patent Publication No. 189295/1986), 6-methyleneandrosta-1,4-diene-3,17-dione derivatives (Japanese Laid-Open Patent Publication No. 12797/1987), 16-oxaandrosta-1,4-diene-3,17-dione (*J. Med. Chem.*, 32, 651, (1989)), etc.

On the other hand, as compounds having chemical structure comparatively analogous to that of the compounds of this invention, there have been known 16-azaandrost-4-ene-3,17-dione and 16-methyl-16-azaandrost-4-en-3-one (*J. Med. Chem.*, 10, 177, (1967)), 17-aza-D-homoandrosta-4,6-diene-3,17a-dione (U.S. Pat. No. 3,642,800), 17a-aza-D-homoandrost-4-en-3-one (*J. Am. Chem., Soc.*, 78, 639, (1956)), 17-oxaandrostan-3-one (*J. Org. Chem.* 49, 3753 (1984)), etc. but there has never been known the use of these compounds as an aromatase inhibitor.

However, known aromatase inhibitors tend to be inactivated by metabolism when administered in living bodies and are not satisfactory for clinical uses.

The present inventors found that a steroidal aromatase inhibitor hard to inactivate by metabolism can be obtained by introducing a hetero atom into the D ring of asteroid.

DISCLOSURE OF INVENTION

The term "lower" in this description means that a group or compound to which this term is attached has 6 or less, preferably 4 or less carbon atoms.

As "lower alkyl groups" in the above formula (I), there can, for example, be mentioned methyl, ethyl, n-propyl, isopropyl, n-butyl, sec-butyl, tert-butyl, n-pentyl, n-hexyl groups, etc., and as halogen atoms there can be mentioned fluorine, chlorine and bromine atoms. "May optionally be acylated or lower alkylated" is the meaning of "may be substituted with an acyl group or a lower alkyl group", and as these "acyl groups" there can be mentioned residue parts obtained by removing at least one OH from organic acids such as mono- or polycarboxylic acids, organic sulfonic acids, and, specifically, groups such as those of the formulae $COR^7$, $-SO_2R^8$, $-COR^9CO-$, etc. are included. Therein $R^7$ denotes a hydrogen atom; a lower alkyl group optionally substituted with a halogen atom, an amino group, a carboxyl group, a lower alkoxycarbonyl group, a lower alkylcarbonyloxy group, a carbamoyl group or an aryl group (for example, a phenyl group, a naphthyl group, etc.); a di-(lower alkyl) amino group; a lower alkenyl group (for example, a vinyl group, a propenyl group, etc.) optionally substituted with an aryl group; a lower cycloalkyl group (for example, a cyclopentyl group, a cyclohexyl group, etc.); or an aryl group optionally substituted with a lower alkyl group, a lower alkoxy group or a halogen atom, $R^8$ denotes a lower alkyl group or an aryl group optionally substituted with a lower alkyl group, and $R^9$ denotes a lower alkylene group, a lower alkenylene group or a phenylene group.

Thus as examples of "a hydroxyl, mercapto or amino group which may optionally be acylated or lower alkylated", there can be mentioned hydroxyl, mercapto, amino, methoxy, ethoxy, acetoxy, propionyloxy, isobutyryloxy, trifluoroacetyloxy, glycyloxy, 3-carboxypropionyloxy, 3-ethoxycarbonylpropionyloxy, acetoxyacetyloxy, phenylacetoxy, acryloyloxy, benzoyloxy, p-methoxybenzoyloxy, methanesulfonyloxy, methylthio, acetylthio, p-methylbenzoylthio, p-chlorobenzoylthio, p-methoxyphenylacetylthio, methylamino, dimethylamino, diethylamino, formylamino, acetylamino, p-toluenesulfonylamino, succinimido, phthalimido groups, etc.

In the above formula (I), as the "lower alkyl group" used in the definition of $R^1$, $R^2$, $R^3$, $R^4$, $R^5$, $R^6$ A and B, a methyl or ethyl group is preferred in each case, as the "halogen atom" used in the definition of $R^2$ a fluorine or chlorine atom is preferred, and as the "halogen atom" used in the definition of $R^3$, $R^4$, $R^5$ and $R^6$ a bromine atom is preferred.

Further, as particularly preferred examples of "acyl" used in the definition of $R^2$ and $R^3$ there can be mentioned lower alkylcarbonyl groups such as acetyl, propionyl and isobutyryl group; arylcarbonyl groups optionally substituted with a lower alkyl group, a lower alkoxy group or a halogen atom such as benzoyl, p-methylbenzoyl, p-methoxybenzoyl and p-chlorobenzoyl; di-(lower alkyl) aminocarbonyl groups such as dimethylaminocarbonyl and diethylaminocarbonyl; etc.

A preferred group of compounds in the above formula (I) are compounds of the formula (I) wherein $R^2$ denotes a hydrogen atom, a halogen atom, a hydroxyl group or an amino group. Further, another preferred group of compounds are compounds of the formula (I) wherein either $R^3$, $R^4$ and $R^5$ each denote a hydrogen atom and $R^6$ denotes a hydrogen atom or a lower alkyl group, or $R^3$ and $R^6$ each denote a hydrogen atom and $R^4$ and $R^5$ combine to denote a single bond, a methylene group or a dihalomethylene group, or $R^3$ and $R^4$ combine to denote an oxo group or a methylene group and $R^5$ and $R^6$ each denote a hydrogen atom.

Still other preferred groups of compounds are compounds of the formula (I) wherein B denotes O, and compounds of the formula (I) wherein X denotes C=O or $CH_2$ and n denotes 2.

In compounds of the formula (I) of this invention, when $R^1$ denotes a lower alkyl group and the 1- and 2-positions of the steroid skeleton are combined by a single bond, the substituent $R^1$ may be bound to any of the α- and β-positions, and when $R^4$ and $R^6$ each denote a halogen atom or a lower alkyl group or when $R^4$ and $R^5$ combine to denote a methylene or dihalomethylene group, each substituent may be bound to any of the α- and β-positions, too.

As representative examples of compounds of the formula (I) provided by this invention, the following ones can be mentioned in addition to those described in later examples.

17-aza-D-homoandrosta-4,6-diene-3,17a-dione,

1α-methyl-16-oxaandrost-4-ene-3,17-dione,

1α-methyl-D-homo-17-oxaandrosta-4,6-diene-3,17-dione,

1α-methyl-D-homo-17-oxaandrosta-1,4,6-triene-3,17a-dione, 4-chloro-D-homo-17-oxaandrost-4-ene-3,17a-dione, 4-fluoro-D-homo-17-oxaandrost-4-ene-3,17a-dione, 4-mercapto-16-oxaandrost-4-ene-3,17-dione, 4-amino-D-homo-17-oxaandrost-4-ene-3,17a-dione, 4-methoxy-D-homo-17-oxaandrost-4-ene-3,17a-dione, 4-methylthio-16-oxaandrost-4-ene-3,17-dione, 4-dimethylamino-D-homo-17-oxaandrost-4-ene-3,17a-dione, 4-acetoxy-16-azaandrost-4-ene-3,17-dione, 4-acetylthio-16-oxaandrost-4-ene-3,17-dione, 4-acetylamino-D-homo- 17-oxaandrost-4-ene-3,17a-dione, 4-hydroxy-D-homo-17-oxaandrosta-1,4-diene-3,17a-dione, 4-hydroxy-16-oxaandrosta-1,4-diene-3,17-dione, 4-mercapto-17-aza-D-homoandrosta-1,4-diene-3,17a-dione, 16-aza-6α-bromoandrost-4-ene-3,17-dione, 6β-chloro-D-homo-17-oxaandrosta-1,4-diene-3,17a-dione, 7α-methyl-16-oxaandrost-4-ene-3,17-dione, 6α-methyl-D-homo-17-oxaandrost-4-ene-3,17a-dione, 7α-methyl-D-homo- 17-oxaandrost-4-ene-3,17a-dione, 16-aza-7α-methylandrosta-1,4-diene-3,17-dione, 6α,7α-methylene-D-homo-17-oxaandrost-4-ene-3,17a-dione, 6α,7α-difluoromethylene-17-aza-D-homoandrost-4-ene-3,17a-dione, 6α,7α-methylene-D-homo-17-oxaandrosta-1,4-diene-3,17 a-dione, 6α,7α-methylene-16-oxaandrosta-1,4-diene-3,17-dione, 6-methylene-16-oxaandrost-4-ene-3,17-dione, 6-methylene-17-aza-D-homoandrosta-1,4-diene-3,17a-dione, D-homo-17-oxaandrosta-1,4-diene-3,6,17a-trione, 17-methyl-17-aza-D-homoandrost-4-ene-3,17a-dione, 4-hydroxy-17-methyl-17-aza-D-homoandrost-4-ene-3,17a-dione, 17-methyl-17-aza-D-homoandrost-4-en-17a-one, 4-chloro-D-homo-17-oxaandrost-4-en-17a-one, D-homo-17-oxaandrosta-4,6-dien-17a-one, 6α,7α-methylene-16-oxaandrost-4-en-17-one, 6α,7α-methylene-D-homo-17-oxaandrost-4-en-17a-one, 6β,7β-methylene-16-azaandrost-4-en-17-one, 6α,7α-difluoromethylene-16-azaandrost-4-en-17-one, 6β,7β-difluoromethylene-D-homo-17-oxaandrost-4-en-17a-one, 6α-bromo-16-azaandrost-4-en-17-one, 7α-methyl-17-aza-D-homoandrost-4-en-17a-one, 17-aza-D-homoandrost-4-ene-6,17a-dione, 6-methylene-D-homo-17-oxaandrost-4-en-17a-one, D-homo-17a-oxaandrosta-1,4-dien-3-one, 17-oxaandrosta-4,6-dien-3-one, D-homo-17a-oxaandrosta-1,4,6-trien-3-one, 1α-methyl-D-homo-17-oxaandrost-4-en-3-one, 1-methyl-D-homo-17-oxaandrosta-1,4-dien-3-one, 4-fluoro-17-oxaandrost-4-en-3-one, 4-mercapto-D-homo-17-oxaandrost-4-en-3-one, 4-amino-17-oxaandrost-4-en-3-one, 4-amino-D-homo-17-oxaandrost-4-en-3-one,
4-methoxy-D-homo-17-oxaandrost-4-en-3-one,
4-dimethylamino-D-homo-17-oxaandrost-4-en-3-one,
4-acetylthio-D-homo-17-oxaandrost-4-en-3-one,
4-acetylamino-D-homo-17-oxaandrosta-4,6-dien-3-one,
4-hydroxy-17-oxaandrosta-1,4-dien-3-one,
4-hydroxy-D-homo-17-oxaandrosta-1,4-dien-3-one,
6α-methyl-D-homo-17-oxaandrost-4-en-3-one,
7α-methyl-17-oxaandrost-4-en-3-one,
7α-ethyl-D-homo-17-oxaandrost-4-en-3-one,
6α,7α-methylene-D-homo-17-oxaandrost-4-en-3-one,
6α,7α-difluoromethylene-17-oxaandrost-4-en-3-one,
6α,7α-difluoromethylene-D-homo-17-oxaandrosta-1,4-dien-3-one,
17-oxaandrosta-1,4-diene-3,6-dione,
D-homo-17-oxaandrosta-1,4-diene-3,6-dione,
6-methylene-16-oxaandrost-4-en-3-one,
6-methylene-17-oxaandrosta-1,4-dien-3-one,
17-oxaandrost-4-ene,
D-homo-17a-oxaandrost-4-ene,
6α,7α-difluoromethylene-17-oxaandrost-4-ene,
7α-methyl-16-oxaandrost-4-ene,
D-homo-17a-oxaandrost-4-en-6-one,
D-homo-17-oxaandrost-4-en-6-one,
6-methylene-D-homo-17-oxaandrost-4-ene.

According to this invention, a compound of the formula (I) wherein symbol A denotes C=O can be prepared either by (a) subjecting, if desired, a compound of the formula

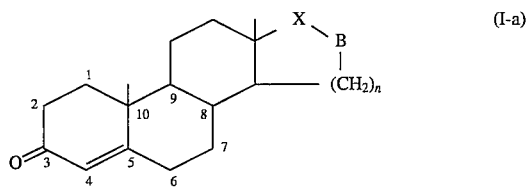
(I-a)

wherein B, X and n are as defined above, obtained by oxidizing and isomerizing a compound of the formula

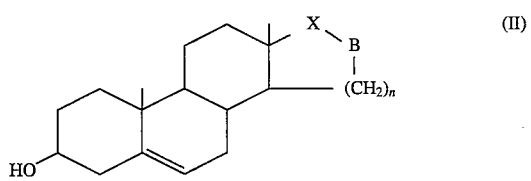
(II)

wherein B, X and n are as defined above, to at least one reaction selected from the reactions of the following (i) to (vii):

(i) a reaction to introduce a double bond between the 1- and 2-positions, (ii) a reaction to introduce a lower alkyl group at the 1-position, (iii) a reaction to introduce a substituent $R^2$ at the 4-position, (iv) a reaction to introduce a double bond between the 6- and 7-positions, (v) a reaction to introduce a halogen atom or a lower alkyl group at the 6- or 7-position, (vi) a reaction to introduce a methylene or dihalomethylene group between the 6- and 7-positions, and (vii) a reaction to introduce an oxo or methylene group at the 6-position, or by (b) subjecting, if desired, a compound of the formula

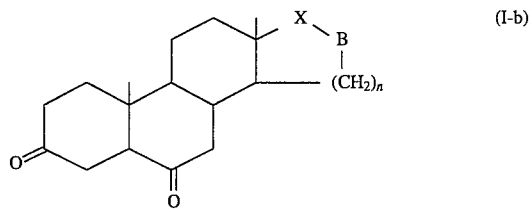
(I-b)

wherein B, X and n are as defined above, obtained by oxidizing a compound of the formula (II) to at least one reaction selected from the reactions of the above (i) to (iii), or (viii) a reaction to convert the 6-position to an acyloxy group.

Further according to this invention, a compound of the formula (I) wherein symbol A denotes $CH_2$ can be prepared by (c) deoxygenation of the 3-position of a compound of the formula

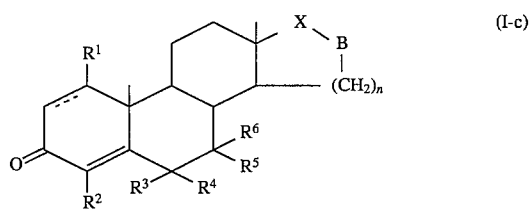
(I-c)

wherein $R^1$, $R^2$, $R^3$, $R^4$, $R^5$, $R^6$, B, X and n are as defined above.

Further according to this invention, a compound of the formula (I) wherein symbol A denotes $C=CH_2$ or C=CH-lower alkyl can be prepared by (d) reacting a compound of the formula (I-c) with Wittig reagent.

In the above process (a), the oxidation of the compound of the formula (II) can be carried out by a process known per se for oxidation of the hydroxyl group(s) of steroid compounds, for example, Oppenauer oxidation, Jones oxidation, Sarett oxidation, Collins oxidation or the like, and the succeeding isomerization can be carried out by treating the resultant compound, usually without isolation, with an acid such as, for example, acetic acid, hydrochloric acid or sulfuric acid.

The oxidation reaction, preferably Oppenauer oxidation can be carried out by treating the compound with a ketone such as cyclohexanone or acetone in the presence of aluminum isopropoxide, aluminum t-butoxide, aluminum phenoxide or the like in an aromatic hydrocarbon such as, for example, benzene, toluene or xylene or a mixed solvent of it with dioxane or the like. Reaction temperature is usually room temperature to the reflux temperature of the reaction mixture, preferably the reflux temperature of the reaction mixture, and as for the use rate of the ketone to the compound of the formula (II), it is advantageous to use the ketone in an amount of the order of 5 to 50 moles per mole of the compound of the formula (II).

In this connection, since Oppenauer oxidation is usually accompanied by an isomerization reaction, it is unnecessary to perform acid treatment, but when the oxidation is carried out with another oxidizing reagent, it is necessary to treat the resultant product with an acid to carry out the isomerization reaction.

Thus a compound of the above formula (I-a) desired in this invention is produced.

The resultant compound of the formula (I-a) can, if desired, be converted to another compound desired in this invention by subjecting it to at least one reaction selected from the reactions of the above (i) to (vii).

In the reaction of the above (i), the introduction of a double bond between the 1- and 2-positions can, usually, be carried out easily by dehydrogenating the compound with 2,3-dichloro-5,6-dicyano-1,4-benzoquinone (DDQ) in dioxane or benzene under reflux.

The introduction of a lower alkyl group at the 1-position in the reaction of the above (ii) can be carried out by lower alkylating the compound wherein a double bond is introduced in advance between the 1- and 2-positions with a lithium lower alkyl copper, for example, lithium dimethyl copper, lithium diethyl copper or the like. Thereby, a 1-lower alkyl-substituted compound wherein the bond between the 1- and 2-positions is a saturated bond is usually obtained.

As for the introduction of the substituent $R^2$ at the 4-position in the reaction of the above (iii), the 4-ene compound is first treated with aqueous hydrogen peroxide generally at a temperature from under ice cooling to room temperature in the presence of an alkali such as sodium hydroxide or potassium hydroxide in a mixed solvent of methanol, t-butanol, dioxane or the like with water to make epoxidation. Then, the resultant 4ξ,5-epoxy compound is treated with an acid, for example, a strong acid such as sulfuric acid, or a mixture of sulfuric acid with an organic acid such as acetic acid or propionic acid to obtain a 4-ene compound wherein a hydroxyl group is introduced at the 4-position; treated with sodium hydrosulfide to obtain a 4-ene compound wherein a mercapto group is introduced at the 4-position; treated with sodium azide and then reduced to obtain a 4-ene compound wherein an amino group is introduced at the 4-position; or treated with a hydrohalogenic acid to obtain a 4-ene compound wherein a halogen atom is introduced at the 4-position. The hydroxyl, mercapto or amino group at the 4-position is acylated or lower alkylated at any time by a process known per se.

In the reaction of the above (iv), the introduction of a double bond between the 6- and 7-positions can, usually, be carried out easily by-dehydrogenating the compound with 2,3,5,6-tetrachloro-1,4-benzoquinone (chloranil) under reflux in t-butanol or xylene.

The introduction of a lower alkyl group at the 6- or 7-position in the reaction of the above (v) can, for example, be carried out either by treating the compound wherein a double bond is introduced in advance between the 6- and 7-positions with a lower alkylmagnesium halide, for example, methylmagnesium iodide in the presence of cuprous chloride in a solvent such as tetrahydrofuran, dioxane or diethyl ether, or by catalytically hydrogenating the compound wherein a methylene group is introduced in advance at the 6-position, and on the other hand, the introduction of a halogen atom at the 6-position can be carried out by treating the compound with a halogenating reagent such as N-halosuccinimide, for example in carbon tetrachloride, if desired under irradiation with light.

The introduction of a methylene group between the 6- and 7-positions in the reaction of the above (vi) can, for example, be carried out either by treating the compound wherein a double bond is introduced in advance between the 6- and 7-positions with methylene iodide in the presence of a zinc-copper couple in a solvent such as diethyl ether or 1,2-dimethoxyethane, or by treating the compound with sodium hydride and trimethylsulfoxonium iodide in dimethylsulfoxide. Further, the introduction of a dihalomethylene group between the 6- and 7-positions can, for example, be carried out usually by treating the compound wherein a double bond is introduced in advance between the 6- and 7-positions with a halocarbene-producing reagent such as sodium chlorodifluoroacetate, sodium trichloroacetate or phenyltribromomethylmercury in an inert solvent such as diethylene glycol dimethyl ether, triethylene glycol dimethyl ether or benzene.

The introduction of a methylene group at the 6-position in the reaction of the above (vii) can, for example, be carried out by treating the compound with an acetal of formaldehyde, for example, diethoxymethane or dimethoxymethane in the presence of an acid such as phosphorus oxychloride, p-toluenesulfonic acid or perchloric acid. Thereby, an alkoxymethyl group is once introduced at the 6-position, but the group is promptly converted to a methylene group with the above acid in the reaction solution. On the other hand, the introduction of an oxo group at the 6-position can, for example, be carried out by oxidation with chromic anhydride.

According to the above process (b), the compound of the formula (I-b) of this invention wherein the 6-position is substituted with an oxo group can also be prepared by oxidizing the compound of the formula (II). This oxidation reaction can, usually, be carried out using Jones reagent.

The resultant compound of the above formula (I-b) can, if desired, be converted to another compound desired in this invention by subjecting it to at least one reaction selected from the reactions of the above (i) to (iii) and (viii).

The conversion to an acyloxy group at the 6-position in the reaction of the above (viii) can easily be carried out by a process known as acylation of a hydroxyl group, for example by treating the compound with an acid chloride, an acid anhydride or the like in pyridine. By this acylation, there can be obtained a compound wherein the 6-position is converted to an acyloxy group and the bond between the 6- and 7-positions is a double bond.

According to the above process (c), by deoxygenation of the 3-position of a compound of the formula (I-c), there can be prepared a compound of the formula (I) of this invention wherein symbol B denotes $CH_2$, namely a compound represented by the formula

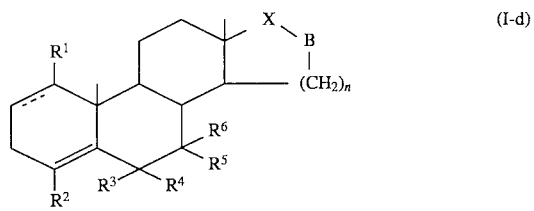

(I-d)

wherein $R^1$, $R^2$, $R^3$, $R^4$, $R^5$, $R^6$, B, X and n are as defined above.

The deoxygenation of the 3-position can be carried out by, first, reacting a compound of the formula (I-c) with an alkanedithiol of the formula

HS—Q—SH  (III)

wherein Q denotes an alkylene group having 2 to 4 carbon atoms,
and reducing the resultant 3-thioketal compound of the formula

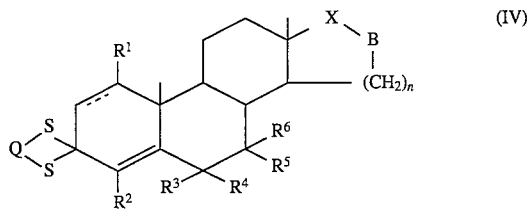

wherein $R^1, R^2, R^3, R^4, R^5, R^6, B, X, n$ and $Q$ are as defined above.

The reaction of the compound of the formula (I-c) with the alkanedithiol of the formula (III) can be carried out by reacting the compound of the formula (I-c) with the alkanedithiol of the formula (III) in the presence of a condensing agent such as p-toluenesulfonic acid or boron trifluoride in a solvent such as, for example, acetic acid, benzene or dioxane at a reaction temperature of about 0° C. to about 100° C.

The amount of the alkanedithiol of the formula (III) to the compound of the formula (I-c) is usually 1 to 1.2 moles per mole of the compound of the formula (I-c), and the amount of the condensing agent is on the order of 0.05 to 0.5 mole per mole of the compound of the formula (I-c).

The resultant 3-thioketal compound of the formula (IV) is then reduced to be converted to a desired compound of the formula (I-d).

The reaction can, for example, be carried out either by treating the 3-thioketal compound with liquid ammonia and an alkali metal such as lithium, sodium or potassium in a solvent such as tetrahydrofuran, ethanol or dioxane, or by treating the compound with Raney nickel in the same solvent as above. The reaction temperature is around −78° C. when liquid ammonia and an alkali metal are used, and is advantageously from room temperature to the reflux temperature of the reaction mixture when Raney nickel is used.

According to the above process (d), a compound of this invention wherein symbol A denotes C=CH$_2$ or C=CH-lower alkyl, namely a compound of the formula

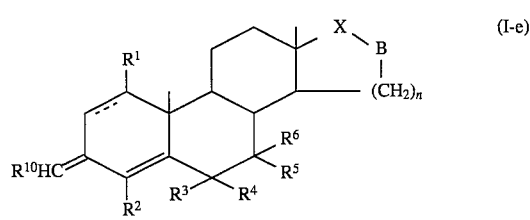

wherein $R^{10}$ denotes a hydrogen atom or a lower alkyl group, and $R^1, R^2, R^3, R^4, R^5, R^6, B, X$ and $n$ are as defined above,
can be prepared by reacting a compound of the above formula (I-c) with a Wittig reagent.

The reaction with the Wittig reagent can be carried out by treating the compound with a lower alkyltriphenylphosphonium halide in the presence of a base such as n-butyl lithium in an inert solvent such as, for example, diethyl ether or tetrahydrofuran, preferably at a reaction temperature around room temperature.

Most of the compounds of the above formula (II) wherein symbol X does not exist or denotes CH$_2$, which are used as a starting material in the above process (a), are novel compounds not disclosed in the literature and can, for example, be prepared by subjecting a compound of the formula

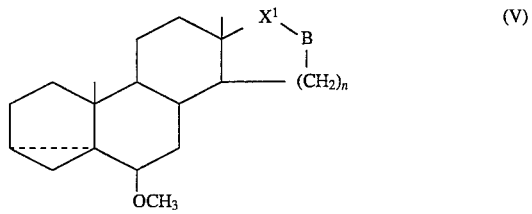

wherein X does not exist or denotes CH$_2$, and n and B are as defined above, to solvolysis.

The solvolysis can easily be carried out by treating the compound with an acid, for example, sulfuric acid, perchloric acid or the like in a mixed solvent of water with dioxane, tetrahydrofuran or the like.

Further, a compound of the above formula (II) wherein x does not exist or denotes CH$_2$ and B denotes O, namely a compound of the formula

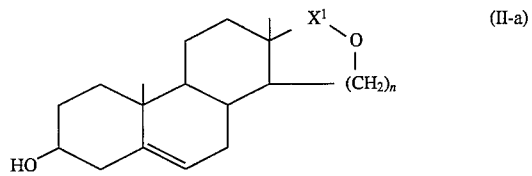

wherein $X^1$ and n are as defined above, can, for example, also be prepared either by
(a) treating a compound of the formula

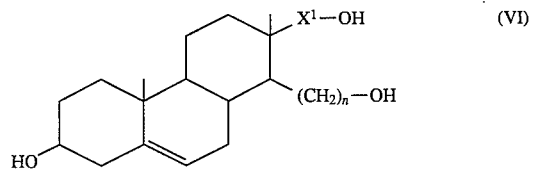

wherein $X^1$ and n are as defined above, with p-toluenesulfonyl chloride, benzenesulfonyl chloride or the like in the presence of a base such as pyridine or triethylamine, or by
(b) reducing a compound of the formula

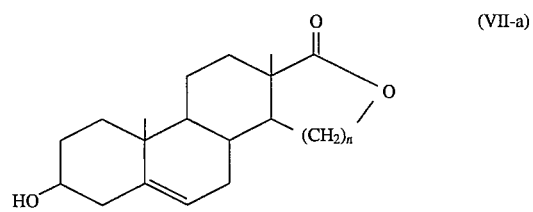

or

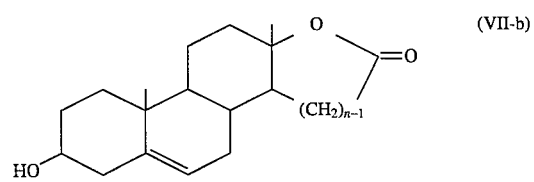

wherein n is as defined above, with tri-tert-butoxyaluminolithium hydride, diisobutylaluminum hydride or the like in a solvent such as tetrahydrofuran, dioxane or toluene to convert the oxo group of the D ring part to a hydroxyl group, and further reducing this hydroxy compound with triethylsilane and boron trifluoride-diethyl ether complex in methylene chloride.

On the other hand, a compound of the formula (II) wherein B denotes NH or N-lower alkyl can also be prepared, for example, by reducing a compound of the formula

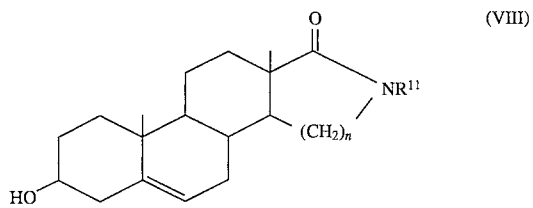

(VIII)

wherein $R^{11}$ denotes a hydrogen atom or a lower alkyl group, and n is as defined above, with lithium aluminum hydride or the like in a solvent such as tetrahydrofuran or dioxane.

Most of the compounds of the formula (V) or (VI) used in the above preparation processes for the starting materials are novel compounds, and the reader is referred to the later-described preparation examples on processes for their preparation. Compounds not disclosed in the preparation processes can also be prepared according to the processes disclosed in the preparation examples.

Thus, the compounds of the above formula (I) prepared according to the processes of this invention can be isolated and purified from the reaction mixtures by means known per se, for example by methods such as recrystallization, distillation, column chromatography and thin layer chromatography.

Uses of the Invention

The thus described oxa- or azasteroid derivatives represented by the formula (I) of this invention have an excellent aromatase inhibition action, and are effective for treatment of diseases caused by excess of estrogens, for example, breast cancer, uterine cancer, ovarian cancer, gynecomastia, prostatic hypertrophy, male infertility based on oligospermia, etc.

The aromatase inhibition actions of compounds of this invention are as follows.

(1) Assay of aromatase inhibition action

According to the method of Ryan (The Journal of Biological Chemistry, 234, 268–272, 1959), human placental microsome (one obtained by centrifugation at 105,000 × g for 60 minutes) was prepared. A microsome was used after being washed twice with 0.5 mM dithiothreitol solution, freeze-dried and stored at −20° C.

Aromatase inhibition action was assayed according to the method developed by Tompson and Siiteri (The Journal of Biological Chemistry, 249, 5373–5378, 1974). The method is to determine the amount of $^3H_2O$ liberated by aromatization of [1,2-$^3$H] androstenedione. The experiment using the enzyme is carried out in 67 mM phosphate buffer of pH 7.5 so that the amount of the last incubation liquid gets to be 0.5 mi. The incubation liquid contains 180 μM NADPH, 2 μM [1,2-$^3$H] androstenedione, 150 μg of the freeze-dried human placental microsome, 25 μl of methanol and a test compound in various concentrations. The incubation is carried out in the air at 37° C. for 20 minutes, 3 ml of chloroform is added to finish the reaction, and then the mixture is stirred for 40 seconds. Then, centrifugation is conducted at 700 × g for 10 minutes, 0.3 ml of the aqueous solution is removed from the supernatant, the scintillation mixture is added, and the amount of $^3H_2O$ formed is determined The results are shown in the following table.

TABLE

| compound | $IC_{50}$ (μM) |
|---|---|
| Example 3 | 1.2 |
| Example 25 | 0.73 |
| Example 28 | 1.3 |
| Example 31 | 0.6 |
| Example 36 | 2.1 |
| Example 50 | 2.7 |
| Example 51 | 2.9 |
| Example 56 | 1.9 |

Thus, the compounds of this invention represented by the formula (I) can be orally or parenterally administered (for example, intramuscular injection, intravenous injection, rectal administration, percutaneous administration, etc.) as an inhibitor of biosynthesis of estrogens for cure or treatment on human or other mammals.

When used as a pharmaceutical, compounds of this invention can be formulated, in accordance with their uses, into any preparation form of solid forms (for example, tablets, hard capsules, soft capsules, granules, powders, fine granules, pills, troches, etc.), semi-solid forms (for example, suppositories, ointments, etc.) and liquid forms (injections, emulsions, suspensions, lotions, sprays, etc.). As nontoxic additives usable for the above preparations, there can, for example, be mentioned starches, gelatin, glucose, lactose, fructose, maltose, magnesium carbonate, talc, magnesium stearate, methylcellulose, carboxymethylcellulose and its salts, gum arabic, polyethylene glycol, p-hydroxybenzoic acid alkyl esters, syrups, ethanol, propylene glycol, vaselines, carbowaxes, glycerol, sodium chloride, sodium sulfite, sodium phosphate, citric acid, etc. These pharmaceuticals can also contain other therapeutically useful pharmaceuticals. The content of the compounds of this invention in the pharmaceuticals can be varied in accordance with their dosage forms, but is desirably in general a concentration of 0.1 to 50 wt. % in the case of solid and semi-solid forms or a concentration of 0.05 to 10 wt. % in the case of liquid forms.

The dose of the compounds of this invention can widely be varied depending on the kind of mammals including human beings as a subject, administration routes, degree of symptoms, diagnoses of doctors, etc., but can generally be 0.1 to 100 mg/kg, preferably 1 to 50 mg/kg per day. However, it is of course possible to administer an amount smaller than the lower limit of the above range or an amount larger than the upper limit in accordance with the above degree of the symptom of the patient and diagnoses of the doctors. The above dose can be administered once or several times with division per day.

EXAMPLES

This invention is further specifically described below according to examples and preparation examples.

Example 1

A mixture of 590 mg of magnesium, 1.8 ml of methyl iodide and 4.6 ml of ether was stirred under a nitrogen stream at room temperature for 1 hour. This mixture was cooled to 0° C. and 90 mg of cuprous chloride and 11 ml of tetrahydrofuran were added. To this mixture was added a mixture of 550 mg of D-homo-17-oxaandrosta-4,6-diene-3,17a-dione, 10 mg of cuprous chloride and 7.3 ml of tetrahydrofuran, and the mixture was stirred for 25 minutes. Ether, water and 5% hydrochloric acid were added to the reaction mixture, and the organic layer was washed with 5% hydrochloric acid, 5% aqueous sodium bicarbonate solution and water, and dried over anhydrous magnesium sulfate. The solvent was distilled out, and the resultant crude product was purified by TLC [developing solvent; chloroform: acetone (9:1)] to obtain 71 mg of 7α-methyl-D-homo-17-oxaandrost-4-ene-3,17a-dione.

$^1$H-NMR (CDCl$_3$, δ) : 0.79 (3H,d,J=6.8Hz), 1.20 (3H,s), 1.27 (3H,s), 4.0–4.7 (2H,m), 5.75 (1H,d,J=1.8Hz)

MS (m/z) : 316 (M$^+$), 301, 274

Example 2

A mixture of 200 mg of methyl 6α,7α-difluoromethylene-16-oxo-16,17-secoandrost-4-en-17-oate, 900 mg of ammonium acetate, 184 mg of sodium cyanoborohydride, 4.9 ml of tetrahydrofuran and 4 ml of methanol was stirred at room temperature for 20 hours. 2 ml of concentrated hydrochloric acid was added to the reaction mixture, and the mixture was stirred for 1 hour. Water was added to the reaction mixture and the product was extracted with chloroform. The extract was washed with 5% aqueous sodium bicarbonate solution and water and dried over anhydrous magnesium sulfate. The solvent was distilled out, and the resultant crude product was purified by TLC [developing solvent; chloroform: acetone (1:1)] to obtain 38 mg of 6α,7α-difluoromethylene-17-aza-D-homoandrost-4-en-17a-one.

$^1$H-NMR (CDCl$_3$, δ): 0.94 (3H,s), 1.21 (3H,s), 3.2–3.6 (2H,m), 5.64 (1H,m), 6.26 (1H,brs)

MS (m/z) : 335 (M$^+$), 320

Example 3

An excess amount of an ethanol suspension of Raney nickel was added to a mixture of 29 mg of 3,3-ethylenedithio-16-oxaandrost-4-en-17-one and 2.9 ml of ethanol, and the mixture was stirred at room temperature for 15 minutes. The insoluble matters were removed from the reaction mixture, the solvent was distilled out, and the resultant crude product was purified by TLC (developing solvent; chloroform) to obtain 20 mg of 16-oxaandrost-4-en-17-one.

$^1$H-NMR (CDCl$_3$, δ): 1.04 (3H,s), 1.12 (3H,s), 3.8–4.4 (2H,m), 5.2–5.4 (1H,brm)

MS (m/z): 274 (M$^+$), 259, 245, 231

Example 4

A mixture of 100 mg of 3β-hydroxy-16-oxaandrost-5-en-17-one, 370 mg of 2,3-dichloro-5,6-dicyano-1,4-benzoquinone and 10 ml of dioxane was refluxed overnight. After completion of the reaction, the insoluble matters were removed by filtration, and the filtrate was flowed into an activated alumina layer and eluted with methylene chloride. The solvent was distilled out, and the resultant crude product was purified by TLC [developing solvent; chloroform: acetone (19:1)] to obtain 48 mg of 16-oxaandrosta-1,4,6-triene-3,17-dione.

$^1$H-NMR (CDCl$_3$, δ): 1.24 (6H,s), 4.0–4.5 (2H,m), 5.82 (1H,brd,J=10Hz), 6.05 (1H,brs), 6.2–6.4 (2H,m), 7.03 (1H, d,J=10Hz)

MS (m/z): 284 (M$^+$), 269, 256, 241

Example 5

415 mg of 16-oxaandrost-4-ene-3,17-dione, 768 mg of 2,3,5,6-tetrachloro-1,4-benzoquinone and 30 ml of t-butanol were refluxed overnight. The insoluble matters were removed from the reaction mixture, the solvent was distilled out, water was added to the residue, and the mixture was extracted with ethyl acetate. The organic layer was washed with 5% aqueous sodium bicarbonate solution, water and saturated saline, and then dried over anhydrous magnesium sulfate. The solvent was distilled out, and the resultant crude product was purified by TLC [developing solvent; chloroform: acetone (39:1)) to obtain 220 mg of 16-oxaandrosta-4,6-diene-3,17-dione.

IR (KBr, cm$^{-1}$); 1776, 1658, 1618, 1262

UV (MeOH, λ$_{max}$); 280 nm $^1$H-NMR (CDCl$_3$, δ): 1.15 (3H,s), 1.21 (3H,s), 4.0–4.6 (2H,m), 5.72 (1H,s), 5.90 (1H,brd,J=10Hz), 6.21 (1H,dd,J=2,10Hz)

MS (m/z): 286 (M$^+$), 271, 268, 258, 242

Example 6

A mixture of 4.92 g of sodium chlorodifluoroacetate and 8.8 ml of triglyme was added dropwise to a mixture of 371 mg of 16-oxaandrosta-4,6-diene-3,17-dione and 7 ml of triglyme under reflux over a period of 30 minutes. The insoluble matters were removed from the reaction mixture by filtration, the solvent was distilled out, and then the residue was extracted with ethyl acetate. The organic layer was washed with water and dried over anhydrous magnesium sulfate. The solvent was distilled out and the resultant residue was crudely purified by silica gel column chromatography [eluent; hexane: acetone (4:1)]. The resultant mixture of products was purified by TLC (developing solvent; chloroform) to obtain 102 mg of 6α,7α-difluoromethylene-16-oxaandrost-4-ene-3,17-dione as the lower polar isomer.

$^1$H-NMR (CDCl$_3$, δ): 1.17 (6H,s), 4.0–4.5 (2H,m), 5.92 (1H,brs)

MS (m/z): 336 (M$^+$), 321, 316, 308, 301, 286

Further, 31 mg of 6β,7β-difluoromethylene-16-oxaandrost-4-ene-3,17-dione was obtained as the higher polar isomer.

$^1$H-NMR (CDCl$_3$, δ): 1.16 (6H,s), 4.0–4.5 (2H,m), 6.00 (1H,s)

Example 7

The procedures of Example 3 were repeated using 10 mg of 3,3-ethylenedithio-6α,7α-difluoromethylene-16-oxaandrost-4-en-17-one in place of 3,3-ethylenedithio-16- oxaandrost-4-en-17-one, and then the crude product was purified by TLC (developing solvent; benzene) to obtain 8 mg of 6α,7α-difluoromethylene-16-oxaandrost-4-en-17-one.

$^1$H-NMR (CDCl$_3$, δ): 0.97 (3H,s), 1.14 (3H,s) 3.9–4.5 (2H,m), 5.5–5.7 (1H,brm)

MS (m/z): 322 (M$^+$), 307, 302, 293, 287

Example 8

The procedures of Example 3 were repeated using 2.3 mg of 3,3-ethylenedithio-6β,7β-difluoromethylene-16-oxaandrost-4-en-17-one in place of 3,3-ethylenedithio-16-oxaandrost-4-en-17-one, and then the crude product was purified by TLC (developing solvent; benzene) to obtain 1.6 mg of 6β,7β-difluoromethylene-16-oxaandrost-4-en-17-one.

¹H-NMR (CDCl₃, δ): 0.97 (3H,d,J=1.5Hz), 1.13 (3H,s), 3.9–4.5 (2H,m), 5.5–5.7 (1H,brm)

MS (m/z): 322 (M⁺), 307, 302, 293, 287

Example 9

A mixture of 18 mg of 6α,7α-difluoromethylene-16-oxaandrost-4-ene-3,17-dione, 18 mg of 2,3-dichloro-5,6-dicyano-1,4-benzoquinone and 0.85 ml of dioxane was refluxed overnight. After completion of the reaction, the insoluble matters were removed by filtration, and the filtrate was flowed into an activated alumina layer and eluted with methylene chloride. The solvent was distilled out, and the resultant crude product was purified by TLC (developing solvent; chloroform) to obtain 8 mg of 6α,7α-difluoromethylene-16-oxaandrosta-1,4-diene-3,17-dione.

¹H-NMR (CDCl₃,δ): 1.20 (3H,s), 1.28 (3H,s), 4.0–4.5 (2H,m), 6.25 (1H,dd,J=2.10Hz), 6.31 (1H,brs), 6.94 (1H,d, J=10 Hz)

MS (m/z): 334 (M⁺), 319, 314, 306

Example 10

A mixture of 100 mg of D-homo-17-oxaandrost-4-ene-3,17a-dione, 30 mg of selenium dioxide, 5 ml of t-butanol and 0.05 ml of acetic acid was refluxed under a nitrogen stream for 48 hours. The insoluble matters were removed by filtration, and the filtrate was distilled out. The product was extracted with ethyl acetate, and the extract was washed with 5% aqueous sodium bicarbonate solution and water, and dried over anhydrous magnesium sulfate. The solvent was distilled out, and the resultant crude product was purified by TLC [developing solvent; chloroform: acetone (19:1)] to obtain 66 mg of D-homo-17-oxaandrosta-1,4-diene-3,17a-dione.

¹H-NMR (CDCl₃,δ): 1.24 (3H,s), 1.29 (3H,s), 4.1–4.7 (2H,m), 6.09 (1H,brs), 6.26 (1H,dd,J=1.8,10.1Hz), 7.04 (1H,d,J=10.1Hz)

MS (m/z): 300 (M⁺), 285, 122

Example 11

53 mg of 3β-hydroxy-16-oxaandrost-5-en-17-one was dissolved in 2.4 ml of acetone and the solution was cooled with ice. 60 μl of Jones reagent was added dropwise to this solution under ice cooling and stirring, and the mixture was stirred for 15 minutes. 2-propanol was added to the reaction mixture and the insoluble matters were removed by filtration. The filtrate was concentrated, water was added and the mixture was extracted with ethyl acetate. The extract was washed with 5% aqueous sodium bicarbonate solution, water and saturated saline, and dried over anhydrous magnesium sulfate. The solvent was distilled out, and the resultant crude product was purified by TLC [developing solvent; chloroform: acetone (19:1)] to obtain 9 mg of 16-oxaandrost-4-ene-3,6,17-trione.

¹H-NMR (CDCl₃, δ): 1.17 (3H,s), 1.22 (3H,s), 3.9–4.4 (2H,m), 6.23 (1H,s)

MS (m/z): 302 (M⁺), 287, 284, 274

Example 12

An acetone suspension of Raney nickel was refluxed for 2 hours. To this suspension was added a solution consisting of 4 mg of 3,3-ethylenedithio-16-oxaandrost-4-ene-6,17-dione in 4 ml of dioxane, and the mixture was refluxed for 1 hour. The insoluble matters were removed from the reaction mixture by filtration, the solvent was distilled out, and the resultant crude product was purified by TLC [developing solvent; benzene: ethyl acetate (4:1)] to obtain 1 mg of 16-oxaandrost-4-ene-6,17-dione.

¹H-NMR (CDCl₃, δ): 1.01 (3H,s), 1.15 (3H,s), 3.9–4.4 (2H,m), 6.47 (1H,t,J=4Hz)

MS (m/z): 288 (M⁺), 273, 270, 260, 255, 245

Example 13

A mixture of 38 mg of 4ξ,5-epoxy-16-oxa-5ξ-androstane-3,17-dione, 0.024 ml of propionic acid and 0.024 ml of sulfuric acid was stirred at room temperature overnight. Water was added to the reaction mixture, and the mixture was extracted with ethyl acetate. The extract was washed with 5% aqueous sodium bicarbonate solution, water and saturated saline, and dried over anhydrous magnesium sulfate. The solvent was distilled out and the resultant crudely purified product was purified by TLC [developing solvent; chloroform: acetone (39:1)] to obtain 33 mR of 4-hydroxy-16-oxaandrost-4-ene-3,17-dione.

¹H-NMR (CDCl₃, δ): 1.15 (3H,s), 1.21 (3H,s), 3.8–4.4 (2H,m), 6.11 (1H,s)

MS (m/z): 304 (M⁺), 302, 290, 289, 276

Example 14

Water was removed from a mixture of 116 mg of dimethylamine hydrochloride, 35.4 mg of paraformaldehyde and 20 ml of isoamyl alcohol by azeotropy. To this mixture was added 30 mR of 16-oxaandrosta-1,4-diene-3,17-dione, and the mixture was refluxed overnight. After being cooled, the mixture was treated with 0.1N aqueous sodium hydroxide solution, and the organic layer was separated and washed with water. The solvent was distilled out, and the resultant crude crystals were washed with hexane and purified by TLC [developing solvent; chloroform: acetone (19:1)] to obtain 1.9 mg of 6-methylene-16-oxaandrosta-1,4-diene-3,17-dione.

¹H-NMR (CDCl₃, δ): 1.18 (6H,s), 3.9–4.4 (2H,m), 5.04 (2H,brd,J=8.5 Hz), 6.19 (1H,brs), 6.26 (1H,dd,J=2,8Hz), 7.03 (1H, d, J=8Hz )

MS (m/z) : 298 (M⁺), 284, 283, 270, 255

Example 15

The procedures of Example 12 were repeated using 10 mg of 3,3-ethylenedithio-16-azaandrost-4-en-17-one in place of 3,3-ethylenedithio-16-oxaandrost-4-ene-6,17-dione, and then the resultant crude product was purified by TLC [developing solvent; chloroform: acetone (19: 1)] to obtain 3 mg of 16 -azaandrost-4-en-17-one.

¹H-NMR (CDCl₃, δ) : 1.04 (6H,s), 2.9–3.4 (2H,m), 5.2–5.4 (1H,br), 5.4–6.0 (1H,br)

MS (m/z) : 273 (M⁺), 258, 244, 230

Example 16

The procedures of Example 4 were repeated using mg of 3β-hydroxy-16-azaandrost-5-en-17-one in place of 3β-hydroxy-16-oxaandrost-5-en -17-one, and then the resultant crude product was purified by TLC [developing solvent; chloroform: acetone (9 :1)] to obtain 34 mg of 16-azaandrosta-1,4,6-triene-3,17-dione.

¹H-NMR (CDCl₃,δ): 1.15 (3H,s), 1.24 (3H,s), 3.1–3.6 (2H,m), 5.5–5.9 (1H,br), 5.89 (1H,dd,J=2,10Hz), 6.04 (1H, brs), 6.2–6.4 (2H,m), 7.05 ( 1H ,d ,J=10Hz)

MS (m/z) : 283 (M⁺), 268, 255, 240

Example 17

The procedures of Example 5 were repeated using mg of 16-azaandrost-4-ene-3,17-dione in place of 16-oxaandrost-4-ene-3,17-dione, and the resultant product was purified by TLC [developing solvent; chloroform: methanol (19:1)] to obtain 57 mg of 16-azaandrosta-4,6-diene-3,17-dione.

$^1$H-NMR (CDCl$_3$, δ): 1.13 (3H,s), 1.15 (3H,s), 3.0–3.6 (2H,m), 5.3–5.7 (1H,br), 5.71 (1H,s), 5.96 (1H,brd,J=10Hz), 6.20 (1H,dd,J=2.5,10Hz)

MS (m/z): 285 (M⁺), 270, 257, 242

Example 18

30 mg of sodium hydride (oily, 60%) was washed three times with petroleum ether and then dried under reduced pressure, and 145 mg of trimethylsulfoxonium iodide was added thereto. 0.8 ml of dimethylsulfoxide was added to this mixture in a nitrogen atmosphere, and the mixture was stirred at room temperature for 30 minutes. 35 mg of 16-azaandrosta-4,6-diene-3,17-dione was added to this mixture, and the mixture was stirred at room temperature for 24 hours. The reaction mixture was poured into ice water and extracted with ethyl acetate. The extract was washed with water and saturated saline, and dried over anhydrous magnesium sulfate. The solvent was distilled out, and the resultant mixture of products was purified by TLC [developing solvent; chloroform: aceton (19:1)] to obtain 4.2 mg of 6α,7α-methylene-16-azaandrost-4-ene-3,17-dione as the lower polar isomer.

$^1$H NMR (CDCl$_3$, δ) : 1.05 (3H,s), 1.11 (3H,s), 3.0–3.7 (2H,m), 5.3–5.9 (1H,br), 6.03 (1H,s)

MS (m/z): 299 (M⁺), 285,284, 271,257, 256

Further, 1.5 mg of 6β,7β-methylene-16-azaandrost-4-ene-3,17-dione was obtained as the higher polar isomer.

$^1$H-NMR (CDCl$_3$, δ): 1.11 (3H,s), 1.17 (3H,s), 3.0–3.7 (2H,m), 5.2–5.8 (1H,br), 5.96 (1H,s),

MS (m/z): 299, 285, 284, 271,257, 256

Example 19

The procedures of Example 9 were repeated using 50 mg of 16-azaandrost-4-ene-3,17-dione in place of 6α,7α-difluoromethylene-16-oxaandrost-4-ene-3,17-dione and the resultant crude product was purified by TLC [developing solvent; chloroform: acetone (19:1)] to obtain 32 mg of 16-azaandrosta-1,4-diene-3,17-dione.

$^1$H-NMR (CDCl$_3$,δ): 1.11 (3H,s), 1.27 (3H,s), 3.0–3.4 (2H,m), 5.2–5.8 ( 1H,br), 6.10 ( 1H,brs), 6.25 (1H,dd,J=2, 10Hz), 7.03 (1H,d,J=10Hz)

MS (m/z): 285 (M⁺), 270, 257, 242

Example 20

The procedures of Example 14 were repeated using 21 mg of 16-azaandrosta-1,4-diene-3,17-dione in place of 16-oxaandrosta-1,4-diene-3,17-dione, and the resultant crude product was purl fie d by TLC [developing solvent; chloroform: methanol (9:1 )] to obtain 2 mg of 6-methylene-16-azaandrosta-1,4-diene-3,17-dione.

$^1$H-NMR (CDCl$_3$, δ): 1.10 (3H,s), 1.18 (3H,s), 3.0–3.4 (2H,m), 5.03 (2H,brd,J=9Hz), 5.3–5.6 (1H,br), 6.17 ( 1H,d, J=2Hz), 6.26 ( 1H,dd,J=2, 10Hz), 7.06 (1H,d,J=10Hz)

MS (m/z) : 297 (M⁺), 282, 269, 254

Example 21

The procedures of Example 13 were repeated using 30 mg of 4ξ,5-epoxy-16-aza-5ξ-androstane-3,17-dione in place of 4ξ,5-epoxy-16-oxa-5ξ-androstane-3,17-dione, and the resultant crude product was purified by TLC [developing solvent; chloroform: me thanol (19:1)] to obtain 14 mg of 4-hydroxy-16-azaandrost-4-ene-3,17-dione.

$^1$H-NMR (CDCl$_3$,δ): 1.07 (3H,s), 1.21 (3H,s), 2.9–3.5 (3H,m), 5.50 (1H,brs), 6.12 (1H,brs)

MS (m/z) : 303 (M⁺), 288, 275, 261,260

Example 22

The procedures of Example 11 were repeated using 3β-hydroxy-16-azaandrost-5-en-17-one in place of 3β-hydroxy-16-oxaandrost-5-en-17-one, and the resultant crude product was purified by TLC [developing solvent; chloroform: acetone (1:1)] to obtain 16-azaandrost-4-ene-3,6,17-trione.

$^1$H-NMR ( CDCl$_3$, δ) : 1.09 (3H,s), 1.21 (3H,s), 2.9–2.5 (2H,m), 6.21 (1H,s), 6.22 (1H,brs)

MS (m/z) : 301 (M⁺), 286, 273

Example 23

A mixture of 47.32 mg of magnesium bromideether complex and 0.44 ml of anhydrous ether was added to a mixture of 18 mg of 5,6α-epoxy-3β-hydroxy-16-aza-5α-androstan-17-one and 0.44 ml of anhydrous benzene, ether was distilled out, and the resultant mixture was refluxed for 5 hours. After being allowed to cool, the organic layer was washed with water, 5% aqueous sodium hydroxide solution, water and saturated saline and dried over anhydrous magnesium sulfate. The solvent was distilled out, and the resultant crude product was purified by TLC [developing solvent; chloroform: methanol (19:1)] to obtain 2.3 mg of 16-azaandrost-4-ene-6,17-dione.

$^1$H-NMR (CDCl$_3$, δ): 1.02 (3H,s), 1.07 (3H,s), 2.9–3.4 (2H,m), 5.3–5.7 (1H,br), 6.46 (1H,t,J=4Hz)

MS (m/z): 287 (M⁺), 272, 269, 259, 254

Example 24

About 1.2 ml of the solvents was distilled out under ordinary pressure from a mixture of 200 mg of 3β-hydroxy-D-homo-17-oxaandrost-5-en-17a-one, 8 ml of dioxane, 7 ml of toluene and 2 ml of cyclohexanone. To this mixture was added a mixture of 200 mg of aluminum isopropoxide and 2 ml of toluene, and the solvents were distilled out while the amount of the contents was maintained to be constant by dropwise addition of toluene. 60 mg of aluminum isopropoxide was added to this reaction mixture, and the mixture was subjected to reaction under the same conditions for 2 hours and refluxed for further 4 hours. The reaction mixture was left to stand at room temperature overnight, 17 ml of 10% aqueous sulfuric acid solution was added, the mixture was stirred for 30 minutes, and the product was extracted with benzene. The extract was washed three times with 10% aqueous potassium carbonate solution, washed with saturated saline, and dried over anhydrous magnesium sulfate. The solvent was distilled out, and the resultant crude product was purified by TLC [developing solvent; chloroform: acetone (19:1)] to obtain 170 mg of D-homo-17-oxaandrost-4-ene-3,17a-dione.

$^1$H-NMR (CDCl$_3$, δ): 1.19 (3H,s), 1.26 (3H,s), 4.1–4.6 (2H,m), 5.75 (1H,s)

MS (m/z) : 302 (M$^+$), 287, 274, 260, 245

Example 25

The procedures of Example 3 were repeated using mg of 3,3-ethylenedithio-D-homo-17-oxaandrost-4-en-17a-one in place of 3,3-ethylenedithio-16-oxaandrost-4-en-17-one, and the resultant crude product was purified by TLC [developing solvent; chloroform: hexane (2:1)] to obtain 59 mg of D-homo-17-oxaandrost-4-en-17a-one.

M.P.: 162°–166° C. (acetone-hexane)

$^1$H-NMR (CDCl$_3$, δ): 1.01 (3H,s), 1.23 (3H,s), 4.0–4.7 (2H,m), 5.32 (1H,m)

MS (m/z) : 228 (M$^+$), 273, 24.5,232

Example 26

The procedures of Example 5 were repeated using mg of D-homo-17-oxaandrost-4-ene-3,17a-dione in place of 16-oxaandrost-4-ene-3,17-dione, and the resultant crude product was purified by TLC [developing solvent; chloroform: acetone (9:1)] to obtain 650 mg of D-homo-17-oxaandrosta-4,6-diene-3,17a-dione.

$^1$H NMR (CDCl$_3$,δ): 1.12 (3H,s), 1.31 (3H,s), 4.1–4.7 (2H,m), 5.71 (1H,s), 6.18 (2H,s)

MS (m/z) : 300 (M$^+$), 285,272, 256

Example 27

The procedures of Example 6 were repeated using mg of D-homo-17-oxaandrosta-4,6-diene-3,17a-dione in place of 16-oxaandrosta-4,6-diene-3,17-dione, and the resultant crude product was purified by TLC [developing solvent; chloroform: acetone (9:1)] to obtain 115 mg of 6α,7α-difluoromethylene-D-homo-17-oxaandrost-4-ene-3,17a-dione as the lower polar isomer.

$^1$H-NMR (CDCl$_3$, δ): 1.13 (3H,s), 1.28 (3H,s), 4.1–4.7 (2H,m), 6.00 (1H,brs)

MS (m/z): 350 (M$^+$), 335, 330, 315, 299

Further, 37 mg of 6β,7β-difluoromethylene-D-homo-17-oxaandrost-4-ene-3,17a-dione was obtained as the higher polar isomer.

$^1$H-NMR (CDCl$_3$, δ): 1.12 (3H,d,J=1.3Hz), 1.26 (3H,s), 4.1–4.7 (2H,m), 5.99 (1H,s)

MS (m/z) : 350 (M$^+$), 335

Example 28

The procedures of Example 3 were repeated using mg of 6β,7α-difluoromethylene-3,3-ethylenedithio-D-homo-17-oxaandrost-4-en-17a-one in place of 3,3-ethylenedithio-16-oxaandrost-4-en-17-one to obtain 25 mg of 6α,7α-difluoromethylene-D-homo-17-oxaandrost-4-en-17a-one.

$^1$H-NMR (CDCl$_3$,δ): 0.94 (3H,s), 1.24 (3H,s), 4.1–4.7 (2H,m), 5.65 (1H,m)

MS (m/z): 336 (M$^+$), 321,301,286

Example 29

The procedures of Example 9 were repeated using 81 mg of 6α,7α-difluoromethylene-D-homo-17-oxaandrost-4-ene-3,17a-dione in place of 6α,7α-difluoromethylene-16-oxaandrost-4-ene-3,17-dione, and the resultant crude product was purified by TLC [developing solvent; chloroform: acetone (9:1)] to obtain 32 mg of 6α,7α-difluoromethylene-D-homo-17-oxaandrosta-1,4-diene-3,17 a-dione.

$^1$H-NMR (CDCl$_3$,δ): 1.25 (3H,s), 1.30 (3H,s), 4.1–4.7 (2H,m), 6.25 (1H,dd,J=2.10Hz), 6.31 (1H,brs), 6.96 (1H,d, J=10Hz)

MS (m/z): 348 (M$^+$), 333, 302

Example 30

The procedures of Example 9 were repeated using 100 mg of D-homo-17-oxaandrosta-4,6-diene-3,17a-dione in place of 6α,7α-difluoromethylene-16-oxaandrost-4-en-3,17-dione, and the resultant product was purified by TLC developing solvent; chloroform: acetone (19:1)] to obtain 16 mg of D-homo-17-oxaandrosta-1,4,6-triene-3,17a-dione.

$^1$H-NMR (CDCl$_3$,δ): 1.20 (3H,s), 1.34 (3H,s), 4.1–4.7 (2H,m), 5.9–6.5 (4H,m), 7.05 (1H,d,J=10.3Hz)

MS (m/z): 298 (M$^+$), 283, 270

Example 31

The procedures of Example 13 were repeated using 800 mg of 4ξ,5-epoxy-D-homo-17-oxa-5ξ-androstane-3,17a-dione in place of 4ξ,5-epoxy-16-oxa-5ξ-androstane-3,17-dione to obtain 423 mg of 4-hydroxy-D-homo-17-oxaandrost-4-ene-3,17a-dione.

M.P. : 229°–232° C. (acetone-hexane)

$^1$H-NMR (CDCl$_3$, δ): 1.18 (3H,s), 1.26 (3H,s), 4.0–4.7 (2H,m), 6.07 (1H,s)

MS (m/z): 318 (M$^+$), 303

Example 32

A mixture of 100 mg of 4-hydroxy-D-homo-17-oxaandrost-4-ene-3,17a-dione, 1 ml of acetic anhydride and 2 ml of pyridine was stirred at room temperature for 18 hours. Water was added to the reaction mixture, and the product was extracted with ethyl acetate. The extract was washed with 5% hydrochloric acid and water, and dried over anhydrous magnesium sulfate. The solvent was distilled out, and the resultant crude product was purified by TLC [developing solvent; chloroform: acetone (19:1)] to obtain 98 mg of 4-acetoxy-D-homo-17-oxaandrost-4-ene-3,17a-dione.

$^1$H-NMR (CDCl$_3$,δ): 1.26 (6H,s), 2.24 (3H,s), 4.0–4.7 (2H,m)

MS (m/z): 360 (M$^+$), 318, 290

Example 33

A mixture of 0.2 ml of thioacetic acid and 0.6 ml of dioxane was added at 0° C. to a mixture of 361 mg of 4ξ,5-epoxy-D-homo-17-oxa-5ξ-androstane-3,17a-dione and 74 ml of dioxane. The mixture was stirred at room temperature for 48 hours, 0.2 ml of thioacetic acid was added, and the mixture was stirred for 3 weeks. Water was added to the reaction mixture, the product was extracted with chloroform, and the extract was washed with 5% aqueous sodium bicarbonate solution and water and dried over anhydrous magnesium sulfate. The solvent was distilled out, and the resultant crude product was purified by TLC [developing solvent; hexane: ethyl acetate (2:1)] to obtain 200 mg of 4-acetylthio-D-homo-17-oxaandrost-4-ene-3,17a-dione.

$^1$H-NMR (CDCl$_3$,δ) : 1.27 (3H,s), 1.29 (3H,s), 2.37 (3H,s), 4.0–4.7 (2H,m)

MS (m/z): 376 (M$^+$), 334

Example 34

An ether solution of hydrogen chloride was added to a mixture of 4-acetylthio-D-homo-17-oxaandrost-4-ene-3,17a-dione and methanol, and the mixture was refluxed under a nitrogen stream for 8 hours. The reaction mixture was cooled, the precipitate was removed by filtration under a nitrogen stream, and the filtrate was distilled. The resultant crude product was purified by TLC [developing solvent; chloroform: acetone (39:1)] to obtain 4-mercapto-D-homo-17-oxaandrost-4-ene-3,17a-dione.

$^1$H-NMR (CDCl$_3$, δ): 1.18 (3H,s), 1.26 (3H,s), 4.0–4.7 (2H,m), 4.74 (1H,s)

Example 35

A mixture of 620 mg of sodium acetate, 18.4 ml of diethoxymethane, 2.4 ml of phosphorus oxychloride and 18.4 ml of chloroform was refluxed for 1 hour. 500 mg of D-homo-17-oxaandrost-4-ene-3,17a-dione was added, and the mixture was further refluxed for 1 hour and brought back to room temperature. Saturated aqueous sodium bicarbonate solution was added dropwise gradually to the reaction mixture to make the pH of the aqueous layer alkaline. The organic layer was washed with water and dried over anhydrous magnesium sulfate. The solvent was distilled out, and the resultant crude product was purified by TLC [developing solvent; chloroform: acetone (19:1)] to obtain 240 mg of 6-methylene-D-homo-17-oxaandrost-4-ene-3,17a-dione.

$^1$H-NMR (CDCl$_3$, δ): 1.09 (3H,s), 1.25 (3H,s), 4.0–4.7 (2H,m), 4.98 (1H,m), 5.11 (1H,m), 5.93 (1H,s)

MS (m/z): 314 (M$^+$), 299, 286, 272

Example 36

The procedures of Example 9 were repeated using 6-methylene-D-homo-17-oxaandrost-4-ene-3,17a-dione in place of 6α,7α-difluoromethylene-16-oxaandrost-4-ene-3,17-dione to obtain 6-methylene-17-oxa-D-homoandrosta-1,4-diene-3,17a-dione.

$^1$H-NMR (CDCl$_3$, δ): 1.14 (3H,s), 1.29 (3H,s), 4.0–4.7 (2H,m), 4.99 (1H,m), 5.07 (1H,m), 6.1–6.4 (2H,m), 7.07 (1H,d,J=10.1Hz)

MS (m/z): 312 (M$^+$), 297, 284, 269

Example 37

A mixture of 9.3 g of cuprous iodide, 54.3 ml of 1.5 M methyl lithium-ether solution and 106 ml of anhydrous ether was stirred under a nitrogen stream at 0° C. for 1 hour. To this was added dropwise over a period of 30 minutes a mixture of 900 mg of D-homo-17-oxaandrost-1,4-diene-3,17a-dione and 18 ml of anhydrous tetrahydrofuran, and the mixture was stirred for further 1.5 hours. The reaction mixture was poured in aqueous ammonium chloride solution, benzene was added, and the mixture was filtered. The organic layer was washed with water and dried over anhydrous magnesium sulfate. The solvent was distilled out, and the resultant crude product was purified by TLC [developing solvent; chloroform acetone (19:1)] to obtain 115 mg of 1α-methyl-D-homo-17-oxaandrost-4-ene-3,17a-dione.

$^1$H-NMR (CDCl$_3$, δ): 0.95 (3H,d,J=6.4Hz), 1.27 (3H,s), 1.28 (3H,s), 4.0–4.7 (2H,m), 5.72 (1H,brs)

MS (m/z): 316 (M$^+$), 301, 274, 259

Example 38

The procedures of Example 9 were repeated using 1α-methyl-D-homo-17-oxaandrost-4-ene-3,17a-dione in place 6α,7α-difluoromethylene-16-oxaandrost-4-ene-3,17of dione, and the resultant crude product was purified by TLC [developing solvent; chloroform: acetone (9:1)] to obtain 1-methyl-D-homo-17-oxaandrosta-1,4-diene-3,17a-dione.

$^1$H-NMR (CDCl$_3$, δ) 1.28 (3H,s), 1.34 (3H,s), 2.14 (3H,d,J=1Hz), 6.08 (1H,brs), 6.19 (1H,brs)

MS (m/z): 314 (M$^+$), 286,271,213

Example 39

The procedures of Example 11 were repeated using 20 mg of 3β-hydroxy-D-homo-17-oxaandrost-5-en-17a-one in place of 3β-hydroxy-16-oxaandrost-5-en-17-one to obtain 11 mg of D-homo-17-oxaandrost-4-ene-3,6,17a-tri-one.

$^1$ H-NMR (CDCl$_3$, δ): 1.17 (3H,s), 1.28 (3H,s), 4.0–4.7 (2H,m), 6.23 (1H,s)

MS (m/z): 316 (M$^+$), 301,298, 288

Example 40

The procedures of Example 3 were repeated using 39 mg of 3,3-ethylenedithio-7α-methyl-D-homo-17-oxaandrost-4-en -17a-one in place of 3,3-ethylenedithio-16-oxaandrost-4-en-17-one to obtain 13 mg of 7α-methyl-D-homo-17-oxaandrost-4-en-17a-one.

$^1$H-NMR (CDCl$_3$, δ) : 0.74 (3H,d,J=6.8Hz), 1.02 (3H,s), 1.23 (3H,s), 4.0–4.7 (2H,m), 5.28 (1H,m)

MS (m/z) : 302 (M$^+$), 287

Example 41

The procedures of Example 12 were repeated using 3,3-ethylenedithio-D-homo-17-oxaandrost-4-ene-6,17a-dione in place of 3,3-ethylenedithio-16-oxaandrost-4-ene-6,17-dione to obtain D-homo-17-oxaandrost-4-ene-6,17a-dione.

$^1$H-NMR (CDCl$_3$, δ): 0.97 (3H,s), 1.26 (3H,s), 4.1–4.7 (2H,m), 6.48 (1H,m)

MS (m/z) : 302 (M$^+$), 287

Example 42

The procedures of Example 24 were repeated using 1.0 g of 3β-hydroxy-17-aza-D-homoandrost-5-en-17a-one in place of 3β-hydroxy-D-homo-17-oxaandrost-5-en-17a-one, and the resultant product was purified by silica gel column chromatography [developing solvent; chloroform: acetone (2:1)] to obtain 847 mg of 17-aza-D-homoandrost-4-ene-3,17a-dione.

$^1$H-NMR (CDCl$_3$, δ): 1.19 (3H,s), 1.21 (3H,s), 3.1–3.5 (2H,m), 5.48 ( 1H,brs), 7.74 (1H,brs)

MS (m/z) : 301 (M$^+$), 286, 259, 244

Example 43

The procedures of Example 3 were repeated using 38 mg of 3,3-ethylenedithio-17-aza-D-homoandrost-4-en-17a-one in place of 3,3-ethylenedithio-16-oxaandrost-4-en-17-one, and the resultant crude product was purified by TLC [developing solvent; ethyl acetate: hexane (2:1)] to obtain 22 mg of 17-aza- D-homoandrost-4-en-17a-one.

$^1$H-NMR (CDCl$_3$, δ): 1.02 (3H,s), 1.18 (3H,s), 3.1–3.5 (2H,m), 5.31 (1H,m), 5.53 (1H,brs)

MS (m/z) : 287 (M+), 272

Example 44

The procedures of Example 9 were repeated using mg of 1 7-aza-D-homoandrost-4-ene-3,17a-dione in place of 6α,7α-difluoromethylene-16-oxaandrost-4-ene-3,17-dione, and the resultant crude product was purified by TLC [developing solvent; chloroform: acetone (9:1)] to obtain 12 mg of 17-aza-D-homoandrosta-1,4-diene-3,17a-dione.

$^1$H-NMR (CDCl$_3$,δ): 1.24 (6H,s), 3.1–3.5 (2H,m), 5.62 (1H,brs), 6.08 ( 1H,brs), 6.25 (1H,dd,J= 2.10Hz), 7.04 (1H,d,J=10Hz)

MS (m/z) : 299 (M+), 284

Example 45

The procedures of Example 13 were repeated using 45 mg of 4ξ,5-epoxy-17-aza-D-homo-5ξ-androstane-3,17a-dione in place of 4ξ,5-epoxy-16-oxa-5ξ-androstane-3,17-dione, and the resultant crude product was purified by TLC [developing solvent; chloroform: acetone (2:1)] to obtain 12 mg of 4-hydroxy-17-aza-D-homoandrost-4-ene-3,17a-dione.

$^1$H-NMR (CDCl$_3$,δ): 1.18 (3H,s), 1.20 (3H,s), 3.1–3.5 (2H,m), 5.63 (1H,brs)

MS (m/z) : 317 (M+), 302

Example 46

The procedures of Example 4 were repeated using 200 mg of 3β-hydroxy-17-aza-D-homoandrost-5-en-17a-one in place of 3β-hydroxy-16-oxaandrost-5-en-17-one, and the resultant crude product was purified by TLC [developing solvent; chloroform: acetone (2:1)] to obtain 37 mg of 17-aza-D-homoandrosta-1,4,6-triene-3,17a-dione.

$^1$H-NMR (CDCl$_3$,δ): 1.20 (3H,s), 1.28 (3H,s) , 3.1–3.7 (2H,m), 5.79 (1H,brs), 5.9–6.5 (4H,m), 7.07 (1H,d,J=10Hz)

MS (m/z) : 297 (M+), 282

Example 47

The procedures of Example 11 were repeated using 3β-hydroxy-17-aza-D-homoandrost-5-en-17a-one in place of 3β-hydroxy-16-oxaandrost-5-en-17-one, and the resultant crude product was purified by TLC [developing solvent; chloroform: acetone (2:1)] to obtain 17-aza-D-homoandrost-4-ene-3,6,17a-trione.

$^1$H-NMR (CDCl$_3$,δ): 1.17 (3H,s), 1.22 (3H,s), 3.38 (2H, m), 5.51 (1H,brs), 6.23 (1H,s)

MS (m/z) : 315 (M+), 300, 287

Example 48

The procedures of Example 11 were repeated using 3β-hydroxy-17-methyl-17-aza-D-homoandrost-5-en-17a-one in place of 3β-hydroxy-16-oxaandrost-5-en-17-one, and the resultant crude product was purified by TLC [developing solvent; chloroform: acetone (4:1)] to obtain 17-methyl-17-aza-D-homoandrost-4-ene-3,6,17a-trione.

$^1$H-NMR (CDCl$_3$, δ): 1.16 (6H,s), 2.89 (3H,s), 3.1–3.5 (2H,m), 6.21 (1H,s)

MS (m/z): 329 (M+), 314, 286

Example 49

30 μl of Jones reagent was added dropwise at 0° C. to a mixture of 10 mg of 16-oxaandrost-5-en-3β-ol and 0.5 ml of acetone, and the mixture was stirred at room temperature for 30 minutes. 2-propanol and 5% aqueous sodium bicarbonate solution were added to the reaction mixture and the insoluble matters were removed by filtration. The filtrate was concentrated under reduced pressure, water was added, and the product was extracted with ethyl acetate. The extract was washed with saturated saline and dried over anhydrous magnesium sulfate. The solvent was distilled out, and the resultant crude product was purified by TLC [developing solvent; chloroform acetone (19:1)] to obtain 3 mg of 16-oxaandrost-4-ene-3,6-dione.

$^1$H-NMR (CDCl$_3$, δ): 1.00 (3H,s), 1.21 (3H,s), 3.3–4.0 (4H,m), 6.21 (1H,s)

MS (m/z): 288 (M+), 273, 270, 260

Example 50

The procedures of Example 49 were repeated using 100 mg of D-homo-17-oxaandrost-5-en-3β-ol in place of 16-oxaandrost-5-en-3β-ol to obtain 24 mg of D-homo-17-oxaandrost-4-ene-3,6-dione.

$^1$H-NMR (CDCl$_3$, δ) : 1.04 (3H,s), 1.17 (3H,s), 3.03,3.43 (2H,ABq,J=11Hz), 3.40 (1H,m), 4.08 (1H,m), 6.20 (1H,s)

MS (m/z): 302 (M+), 287, 284, 274

Example 51

A mixture of 100 mg of D-homo-17-oxaandrost-5-en-3β-ol, 350 mg of 2,3-dichloro-5,6-dicyano-1,4-benzoquinone and 10 ml of dioxane was refluxed for 30 hours. After completion of the reaction, the insoluble matters were removed by filtration, and the filtrate was poured into an activated alumina layer and eluted with methylene chloride. The solvent was distilled out, and the resultant crude product was purified by TLC [developing solvent; chloroform: acetone (19:1)] to obtain 25 mg of D-homo-17-oxaandrosta-1,4,6-trien-3-one.

$^1$H-NMR (CDCl$_3$,δ): 1.10 (3H,s), 1.19 (3H,s), 3.02,3.43 (2H,ABq,J=11Hz), 3.40 (1H,m), 4.10 (1H,m), 6.03 (1H,s), 6.1–6.4 (3H,m), 7.03 (1H,d,J=10Hz)

MS (m/z) : 284 (M+)

Example 52

About 1.2 ml of the solvents were distilled out under ordinary pressure from a mixture of 200 mg of D-homo-17-oxaandrost-5-en-3β-ol, 8 ml of dioxane, 7 ml of toluene and 2 ml of cyclohexanone. A mixture of 250 mg of aluminum isopropoxide and 2 ml of toluene was added to this mixture, and the solvents were distilled out for 30 minutes while the amount of the contents was maintained to be constant by dropwise addition of toluene. 300 mg of aluminum isopropoxide was added to this reaction mixture, and the mixture was subjected to reaction under the same conditions for 2 hours and then refluxed for 4 hours. The reaction mixture was allowed to stand at room temperature overnight, 16 ml of 10% aqueous sulfuric acid solution was added, the mixture was stirred for 30 minutes, and the product was extracted with benzene. The extract was washed three times with 10% aqueous potassium carbonate solution, washed with saturated saline, and dried over anhydrous magnesium sulfate. The solvent was distilled out, and the resultant crude product was purified by TLC [developing solvent; chloroform: acetone (19:1)] to obtain 155 mg of D-homo-17-oxaandrost-4-en-3-one.

$^1$H-NMR (CDCl$_3$, δ): 1.03 (3H,s), 1.19 (3H,s) 2.97,3.39 (2H,ABq,J=11Hz), 3.35 (1H,m), 4.05 (1H,m), 5.73 (1H,s)

MS (m/z): 288 (M⁺), 246

Example 53

A mixture of 20 mg of D-homo-17-oxaandrost-4-en-3-one, 6 mg of selenium dioxide, 0.01 ml of acetic acid and 1 ml of t-butanol was refluxed under a nitrogen stream for 48 hours. The insoluble matters were removed by filtration from the reaction mixture, and the solvent was distilled out. Water was added to the residue, and the product was extracted with ethyl acetate. The extract was washed with 5% aqueous sodium bicarbonate solution and saturated saline, and dried over anhydrous magnesium sulfate. The solvent was distilled out, and the resultant crude product was purified by TLC [developing solvent; chloroform: acetone (19:1)] to obtain 17 mg of D-homo-17-oxaandrosta-1,4-dien-3-one.

$^1$H-NMR (CDCl$_3$, δ): 1.06 (3H,s), 1.24 (3H,s) 2.97,3.39 (2H,ABq,J=11Hz), 3.35 (1H,m), 4.05 (1H,m), 6.08 (1H,brs), 6.25 (1H,dd,J=2.10Hz), 7.03 (1H,d,J=10Hz)

MS (m/z) : 286 (M⁺)

Example 54

A mixture of 300 mg of 4ξ,5-epoxy-D-homo-17-oxa-5ξ-androstan-3-one, 1.03 g of sodium azide, 0.075 ml of concentrated sulfuric acid and 5.1 ml of dimethyl sulfoxide was heated at 100° C. for 1 hour. 3% hydrochloric acid was added to the cooled reaction mixture, and the mixture was stirred for 15 minutes. The insoluble matters were removed by filtration and the filtrate was washed with diethyl ether. 2N aqueous sodium hydroxide solution was added to the filtrate, and the precipitated crystals were collected by filtration, washed with water and vacuum dried to obtain 85 mg of 4-amino-D-homo-17-oxaandrosta-4,6-dien-3-one.

$^1$H-NMR (CDCl$_3$, δ): 1.07 (6H,s), 3.03,3.43 (2H,ABq,J=11Hz), 3.0–4.0 (3H,m), 4.1 (1H,m), 6.0–6.7 (2H,m)

MS (m/z): 301 (M⁺), 286, 258

Example 55

A mixture of 97 mg of 4ξ,5-epoxy-D-homo-17-oxa-5ξ-androstan-3-one, 4 ml of 18% hydrogen chloride-2-propanol solution and 4 ml of ethyl acetate was stirred at room temperature for 1 hour. The solvent was distilled out, and the resultant crude product was purified by TLC [developing solvent; n-hexane : ethyl acetate (5:1)] to obtain 65 mg of 4-chloro-D-homo-17-oxaandrost-4-en-3-one.

$^1$H-NMR (CDCl$_3$,δ): 1.03 (3H,s), 1.23 (3H,s) 2.97,3.39 (2H,ABq,J=11Hz), 3.35 (1H,m), 4.05 (1H,m)

MS (m/z) : 322 (M⁺), 286, 245

Example 56

A mixture of 25 mg of 4ξ,5-epoxy-D-homo-17-oxa-5ξ-androstan-3-one, 0.02 ml of concentrated sulfuric acid and 0.15 ml of propionic acid was stirred at room temperature for 5 hours. Water was added to the reaction mixture and the product was extracted with ethyl acetate. The extract was washed with 5% aqueous sodium bicarbonate solution and saturated saline and dried over anhydrous magnesium sulfate. The solvent was distilled out, and the resultant crude product was purified by TLC [developing solvent; chloroform: acetone (19:1)] to obtain 15 mg of 4-hydroxy-D-homo-17-oxaandrost-4-en-3-one.

$^1$H-NMR (CDCl$_3$,δ): 1.02 (3H,s), 1.18 (3H,s) 2.97,3.39 (2H,ABq,J=11Hz), 3.35 (1H,m), 4.05 (1H,m), 6.05 (1H,s)

MS (m/z) : 304 (M⁺)

Example 57

A mixture of 400 mg of 3,3-ethylenedithio-D-homo-17-oxaandrost-4-ene, Raney nickel and 150 ml of ethanol was stirred at room temperature for 30 minutes. The insoluble matters were removed by filtration, the solvent was distilled out, and the resultant crude product was purified by TLC [developing solvent; n-hexane: ethyl acetate (5:1)] to obtain 195 mg of D-homo-17-oxaandrost-4-ene.

$^1$H-NMR (CDCl$_3$, δ): 1.00 (3H,s), 1.01 (3H,s) 2.97,3.36 (2H,ABq,J=11Hz), 3.35 (1H,m), 4.05 (1H,m), 5.30 (1H,m)

MS (m/z) : 274 (M⁺), 259

Example 58

A mixture of 1.3 g of D-homo-17-oxaandrost-4-en-3-one, 2.7 g of 2,3,5,6-tetrachloro-1,4-benzoquinone and 66 ml of tert-butanol was refluxed for 5 hours. The insoluble matters were removed from the reaction mixture and the solvent was distilled out. Water was added to the residue and the product was extracted with ethyl acetate. The extract was washed with 5% aqueous sodium hydroxide solution and saturated saline and dried over anhydrous magnesium sulfate. The solvent was distilled out, and the resultant crude product was purified by TLC [developing solvent; chloroform: acetone (19:1) ] to obtain 809 mg of D-homo-17-oxaandrosta-4,6-dien-3-one.

$^1$H NMR (CDCl$_3$, δ): 1.07 (3H,s), 1.12 (3H,s) 3.02,3.41 (2H,ABq,J=11Hz), 3.40 (1H,m), 4.10 (1H,m), 5.68 (1H,s ), 6.18 (2H,s)

MS (m/z) : 286 (M⁺)

Example 59

A mixture of 107 mg of magnesium, 0.33 ml of methyl iodide and 0.8 ml of diethyl ether was stirred under a nitrogen stream at room temperature for 1 hour. This mixture was cooled to 0° C., and 16 mg of cuprous chloride and 2 ml of tetrahydrofuran were added. To this mixture were added a mixture of 100 mg of D-homo-17-oxaandrosta-4,6-dien-3-one, 5 mg of cuprous chloride and 1.3 ml of tetrahydrofuran, and the mixture was stirred for 25 minutes. Diethyl ether, water and 5% hydrochloric acid were added to the reaction mixture, the organic layer was washed with 5% aqueous sodium hydroxide solution and saturated saline, and dried over anhydrous sodium sulfate. The solvent was distilled out, and the resultant crude product was purified by TLC [developing solvent; benzene: ethyl acetate ( 19: 1 ) ] to obtain 66 mg of 7 -methyl-D-homo-17-oxaandrost-4-en-3-one as the lower polar isomer.

$^1$H-NMR (CDCl$_3$, δ): 0.7 4 (3H,d,J=7Hz), 1.03 (3H,s) 1.19 (3H,s), 3.00,3.39 (2H ,ABq,J=11Hz), 3.40 (1H,m) , 4.05 ( 1H,m), 5.73 ( 1H,d,J =2Hz)

MS (m/z) : 302 (M⁺), 26

Further, 14 mg of 7B-methyl-D-homo-17-oxaandrost-4-en-3-one was obtained a s the higher polar isomer.

$^1$H-NMR (CDCl$_3$,δ): 1.04 (3H,s), 1.10 (3H,d,J=6Hz), 1.16 (3H,s), 2.99,3.39 (2H,ABq,J=11Hz), 3.35 (1H,m), 4.05 (1H,m), 5.72 (1H,brs)

MS (m/z) 302 (M⁺), 260

Example 60

The procedures of Example 57 were repeated using 80 mg of 3,3-ethylenedithio-7α(-methyl-D-homo-17-oxaandrost-4-ene in place of 3,3-ethylenedithio-D-homo-17-oxaandrost-4-ene to obtain 30 mg of 7α-methyl-D-homo-17-oxaandrost-4-ene.

$^1$H-NMR (CDCl$_3$ δ): 0.70 (3H,d,J=7Hz), 1.00 (3H,s), 1.02 (3H,s), 2.98,3.37 (2H,ABq,J=11Hz), 3.35 (1H,m), 4.05 (1H,m), 5.25 (1H,m)

MS (m/z): 288 (M$^+$), 273

Example 61

A mixture of 3.3 g of sodium chlorodifluoroacetate and 8.4 ml of triglyme was added dropwise to a mixture of 296 mg of D-homo-17-oxaandrosta-4,6-dien-3-one and 5.3 ml of triglyme under reflux over a period of 30 minutes, and the mixture was refluxed for 30 minutes. The insoluble matters were removed from the reaction mixture by filtration, the solvent was distilled out, and the product was extracted with diethyl ether. The extract was washed with saturated saline and dried over anhydrous sodium sulfate. The solvent was distilled out, and the resultant crude product was purified by TLC [developing solvent; n-hexane: ethyl acetate (4:1)] to obtain 56 mg of 6α,7α(-difluoromethylene-D-homo-17-oxaandrost-4-en-3-one as the lower polar isomer.

$^1$H-NMR (CDCl$_3$ δ): 1.05 (3H,s), 1.13 (3H,s) 3.02,3.41 (2H,ABq,J=11Hz), 3.40 (1H,m), 4.10 (1H,m), 5.98 (1H,s)

MS (m/z): 336 (M$^+$), 321,301,285

Further, 7 mg of 6β,7β-difluoromethylene-D-homo-17-oxaandrost-4-en-3-one was obtained as the higher polar isomer.

$^1$H-NMR (CDCl$_3$ δ): 7.02 (3H,s), 1.13 (3H,d,J=1Hz), 3.03,3.45 (2H,ABq,J=11Hz), 3.45 (1H,m), 4.12 (1H,m), 5.97 (1H,s)

MS (m/z): 336 (M$^+$), 321,301,285

Example 62

The procedures of Example 57 were repeated using 14 mg of 6α,7α-difluoromethylene-3,3-ethylenedithio-D-homo-17-oxaandrost-4-ene in place of 3,3-ethylenedithio-D-homo-17-oxaandrost-4-ene to obtain 8 mg of 6α,7α-difluoromethylene-D-homo-17-oxaandrost-4-ene.

$^1$H-NMR (CDCl$_3$ δ): 0.94 (3H,s), 1.01 (3H,s), 3.00,3.39 (2H,ABq,J=11Hz), 3.42 (1H,m), 4.08 (1H,m), 5.62 (1H,m)

MS (m/z) : 322 (M$^+$), 307

Example 63

A mixture of 30 mg of 6α,7α-difluoromethylene-3,3-ethylenedithio-D-homo-17-oxaandrost-4-ene and 0.7 ml of tetrahydrofuran was added to a mixture of 60 mg of sodium metal and 4.3 ml of liquid ammonia, and the mixture was stirred at −78° C. for 30 minutes. The greater part of the ammonia was removed from the reaction mixture, saturated aqueous ammonium chloride solution and 5% hydrochloric acid were added, and the product was extracted with ethyl acetate. The extract was washed with 5% aqueous sodium bicarbonate solution and saturated saline, and dried over anhydrous magnesium sulfate. The solvent was distilled out, and the resultant crude product was purified by TLC [developing solvent; n-hexane: ethyl acetate (5:1)] to obtain 2 mg of 6α,7α(-methylene-D-homo-17-oxaandrost-4-en-3-one.

$^1$H-NMR (CDCl$_3$ δ): 0.97 (3H,s), 1.03 (3H,s) 2.98,3.37 (2H,ABq,J=11Hz), 3.40 (1H,m), 4.05 (1H,m), 5.50 (1H,m)

MS (m/z): 286 (M$^+$), 271

Example 64

A mixture of 62 mg of sodium acetate, 1.8 ml of diethoxymethane, 0.24 ml of phosphorus oxychloride and 1.8 ml of chloroform was stirred for 1 hour. 50 mg of D-homo-17-oxaandrost-4-en-3-one was added, and the mixture was refluxed for further 1 hour and brought back to room temperature. Saturated aqueous sodium bicarbonate solution was added dropwise gradually to the reaction mixture to make the pH of the aqueous layer alkaline. The organic layer was washed with saturated saline and dried over anhydrous magnesium sulfate. The solvent was distilled out, and the resultant crude product was purified by TLC [developing solvent; chloroform: acetone (100:1) ] to obtain 30 mg of 6-methylene-D-homo-17-oxaandrost-4-en-3-one.

$^1$H-NMR (CDCl$_3$ δ): 1.02 (3H,s), 1.09 (3H,s) 3.00,3.40 (2H,ABq,J=11Hz), 3.40 (1H,m), 4.08 (1H,m), 4.94 (1H,m), 5.07 (1H,m), 5.91 (1H,s)

MS (m/z): 300 (M$^+$), 285,272, 258

Example 65

A mixture of 26 mg of 6-methylene-D-homo-17-oxaandrost-4-en-3-one, 26 mg of 2,3-dichloro-5,6-dicyano-1,4-benzoquinone and 1 ml of dioxane was refluxed for 9 hours. The reaction mixture was flowed into an activated alumina layer and eluted with methylene chloride. The solvent was distilled out, and the resultant crude product was purified by TLC [developing solvent; chloroform: acetone (100:1)] to obtain 6-methylene-D-homo-17-oxaandrosta-1,4-dien-3-one.

$^1$H-NMR (CDCl$_3$ δ): 1.05 (3H,s), 1.14 (3H,s) 3.00,3.42 (2H,ABq,J=11Hz), 3.40 (1H,m), 4.10 (1H,m), 4.95 (1H,m), 5.02 (1H,m), 6.16 (1H,m), 6.27 (1H,dd,J=2,10Hz), 7.07 (1H,d,J=10Hz)

MS (m/z) : 298 (M$^+$), 283

Example 66

The procedures of Example 49 were repeated using 40 mg of 17-oxaandrost-5-en-3β-ol in place of 16-oxaandrost-5-en-3B-ol to obtain 18 mg of 17-oxaandrost-4-ene-3,6-dione.

$^1$H-NMR (CDCl$_3$ δ): 1.03 (3H,s), 1.17 (3H,s), 3.7–4.1 (2H,m), 6.21 (1H,s)

MS (m/z) : 288 (M$^+$), 273

Example 67

0.2 ml of Jones reagent was added dropwise at 0° C. to a mixture of 203 mg of 17-oxaandrost-5-en-3β-ol and 20 ml of acetone, and the mixture was stirred for 20 minutes. Water was added to the reaction mixture and the product was extracted with ethyl acetate. The extract was washed with 5% aqueous sodium bicarbonate solution and saturated saline, and dried over anhydrous magnesium sulfate. The solvent was distilled out, and the resultant 17-oxaandrost-5-en-3-one was dissolved in 10 ml of acetone. After addition of 0.01 ml of concentrated sulfuric acid, the reaction mixture was stirred at room temperature for 2 hours. Water was added to the reaction mixture and the product was extracted with ethyl acetate. The extract was washed with 5% aqueous sodium bicarbonate solution and saturated saline, and dried over anhydrous magnesium sulfate. The solvent was distilled out, and the resultant product was purified by TLC [developing solvent; chloroform: acetone (9:1)] to obtain 102 mg of 17-oxaandrost-4-en-3-one.

$^1$H-NMR (CDCl$_3$,δ): 1.01 (3H,s), 1.19 (3H,s), 3.7–4.1 (2H,m), 5.74 (1H,brs)

MS (m/z) : 274 (M$^+$), 259

Example 68

The procedures of Example 65 were repeated using 50 mg of 17-oxaandrost-4-en-3-one in place of methylene-D-homo-17-oxaandrost-4-en-3-one, and the resultant crude product was purified by TLC [developing solvent; chloroform: acetone (39:1)] to obtain 25 mg of 17-oxaandrosta-1,4-dien-3-one.

$^1$H-NMR (CDCl$_3$, δ): 1.04 (3H,s), 1.23 (3H,s), 3.7–4.1 (2H,m), 6.09 (1H,brs), 6.25 (2H,dd,J=2,10Hz), 7.01 (1H,d, J=10Hz)

MS (m/z) : 272 (M$^+$), 257

Example 69

The procedures of Example 56 were repeated using 49 mg of 4ξ,5-epoxy-17-oxa-5ξ-androstan-3-one in place of 4ξ,5-epoxy-D-homo-17-oxa-5ξ-androstan-3-one to obtain 22 mg of 4-hydroxy-17-oxaandrost-4-en-3-one.

$^1$H-NMR (CDCl$_3$, δ) : 1.01 (3H,s), 1.17 (3H,s), 3.7–4.1 (2H,m), 6.08 (1H,s)

MS (m/z) : 290 (M$^+$), 275

Example 70

The procedures of Example 49 were repeated using 100 mg of D-homo-17a-oxaandrost-5-en-3β-ol in place of 16-oxaandrost-5-en-3β-ol, and the resultant product was purified by TLC [developing solvent; chloroform: acetone (39:1)] to obtain 27 mg of D-homo-17a-oxaandrost-4-ene-3,6-dione.

$^1$H-NMR (CDCl$_3$,δ) : 1.13 (3H,s), 1.20 (3H,s), 3.6–3.8 (2H,m), 6.20 (1H,s)

MS (m/z) : 302 (M$^+$), 287

Example 71

By refluxing a mixture of 15 mg of lithium aluminum hydride and 3 ml of diethyl ether using a Soxhlet extractor, 15 mg of 17-aza-D-homoandrost-4-en-17a-one was extracted. The resultant reaction mixture was refluxed for 24 hours, 0.1 ml of water was added, and the mixture was refluxed for 1 hour. The insoluble matters were removed from the reaction mixture by filtration, the solvent was distilled out, and the resultant crude product was purified by alumina column chromatography [eluent; chloroform: methanol (9:1)] to obtain 10 mg of 17-aza-D-homoandrost-4-ene.

$^1$H-NMR (CDCl$_3$,δ): 1.01 (3H,s), 1.18 (3H,s), 5.30 (1H, m)

MS (m/z) : 273 (M$^+$), 258, 230, 215

Example 72

The procedures of Preparation example 31 were repeated using 90 mg of 17aξ-hydroxy-D-homo-17-oxaandrost-4-en-3-one in place of D-homo-17-oxaandrost-5-ene-3β,17aξ-diol to obtain 70 mg of D-homo-17-oxaandrost-4-en-3-one.

Example 73

A mixture of 4 mg of 4-hydroxy-D-homo-17-oxaandrost-4-en-3-one, 0.5 ml of pyridine and 0.25 ml of acetic anhydride was stirred at room temperature for 15 hours. Water was added to the reaction mixture and the product was extracted with ethyl acetate. The extract was washed with 3% hydrochloric acid, 5% aqueous sodium bicarbonate solution and saturated saline, and dried over anhydrous magnesium sulfate. The solvent was distilled out to obtain 4 mg of 4-acetoxy-D-homo-17-oxaandrost-4-en-3-one.

$^1$H-NMR (CDCl$_3$,δ): 1.02 (3H,s), 1.25 (3H,s), 2.23 (3H, s), 2.97,3.40 (2H,ABq,J=11Hz), 3.35 (1H,m), 4.05 (1H,m)

MS (m/z): 346 (M$^+$), 304

Example 74

A mixture of 40 mg of D-homo-17-oxaandrost-4-ene-3,6,17a-trione, 20 mg of acetyl chloride and 0.8 ml of pyridine was stirred at room temperature for 20 hours. 4 ml of 0.1 N hydrochloric acid was added to the reaction mixture and the product was extracted twice with 10 ml of ethyl acetate. The extract was washed with saturated saline and dried over anhydrous sodium sulfate. The solvent was distilled out, and the resultant product was purified by TLC [developing solvent; n-hexane : ethyl acetate (1:1)] to obtain 40 mg of 6-acetoxy-D-homo-17-oxaandrosta-4,6-diene-3,17a-dione.

$^1$H-NMR (CDCl$_3$,δ): 1.19 (3H,s), 1.31 (3H,s), 2.21 (3H, s), 4.1–4.7 (2H,m), 5.84 (1H,s), 5.84 (1H,d,J=2Hz)

MS (m/z) : 358 (M$^+$), 316, 301,288

Example 75

The procedures of Example 74 were repeated using 20 mg of propionic anhydride in place of acetyl chloride to obtain 30 mg of 6-propionyloxy-D-homo-17-oxaandrosta-4,6-diene-3,17a-dione.

$^1$H-NMR (CDCl$_3$, δ) : 1.19 (3H,t,J=6.5Hz), 1.20 (3H,s), 1. 31 (3H,s), 2.51 (2 H,q,J=6.5Hz), 4.1–4.7 (2H,m), 5.83 (1H,s ), 5.88 (1H,d,J=2Hz)

MS (m/z) : 372 (M$^+$), 316, 301,288

Example 76

The procedures of Example 74 were repeated using 20 mg of isobutyryl chloride in place of acetyl chloride to obtain 41 mg of 6-isobutyryloxy-D-homo-17-oxaandrosta-4,6-diene-3,17a-dione.

$^1$H-NMR (CDCl$_3$, δ): 1.20 (3H,s), 1.27 (6H,d,J=7Hz), 1.31 (3H,s), 2.73 ( 1H,sep,J=7Hz), 4.1–4.7 (2H,m), 6.7–6.9 (2 H,m)

MS (m/z) : 386 (M$^+$), 316, 288

Example 77

The procedures of Example 74 were repeated using 20 mg of benzoyl chloride in place of acetyl chloride to obtain 50 mg of 6-benzoyloxy-D-homo-17-oxaandrosta-4,6-diene-3,17a-dione.

$^1$H-NMR (CDCl$_3$, δ): 1.27 (3H,s), 1.34 (3H,s), 4.1–4.7 (2H,m), 5.92 (1H,s), 6.03 (1H,d,J=2Hz), 7.4–7.8 (3H,m), 8.0–8.2 (2H,m)

MS (m/z): 420 (M$^+$), 405, 392, 298

Example 78

A mixture of 35 mg of D-homo-17-oxaandrost-4-ene-3,6,17a-trione, 14 mg of N,N-dimethylcarbamoyl chloride and 0.2 ml of pyridine was stirred at 100° C. for 24 hours. 4 ml of 0.1N hydrochloric acid was added to the reaction mixture and the product was extracted twice with 10 ml of ethyl acetate. The extract was washed with saturated saline and dried over anhydrous sodium sulfate. The solvent was distilled out, and the resultant crude product was purified by TLC [developing solvent; chloroform: acetone (19:1)] to obtain 37 mg of 6-(N,N-dimethylcarbamoyloxy)-D-homo-17-oxaandrosta-4,6-diene-3,17a -dione.

$^1$H-NMR (CDCl$_3$, δ): 1.21 (3H,s), 1.31 (3H,s), 2.95 (3H,s), 3.03 (3H,s), 4.1–4.7 (2H,m), 5.87 (1H,s), 5.92 (1H, d,J=2Hz)

MS (m/z): 387 (M$^+$), 72

Example 79

2.04 ml of 15% n-butyl lithium-n-hexane solution was added to a mixture of 1.45 g of methyltriphenylphosphonium bromide and 77 ml of diethyl ether, and the mixture was stirred under a nitrogen stream at room temperature for 30 minutes. To this mixture were added 300 mg of D-homo-17-oxaandrost-4-en-3-one and 100 ml of diethyl ether, and the mixture was stirred at room temperature for 5 minutes. Water was added to the reaction mixture and the product was extracted with ethyl acetate. The extract was washed with saturated saline and dried over anhydrous sodium sulfate. The solvent was distilled out, and the resultant crude product was purified by TLC [developing solvent; n-hexane: ethyl acetate (9:1)] to obtain 220 mg of 3-methylene-D-homo-17-oxaandrost-4-ene.

$^1$H-NMR (CDCl$_3$,δ) : 1.00 (3H,s), 1.05 (3H,s), 2,96,3,37 (2H,ABq,J=11Hz), 3.35 (1H,m), 4.05 (1H,m), 4.65 (2H,m), 5.82 (1H,brs)

MS (m/z) : 286 (M$^+$), 271

Example 80

The procedures of Example 79 were repeated using 17-aza-D-homoandrost-4-ene-3,17a-dione and tetrahydrofuran in place of D-homo-17-oxaandrost-4-en-3-one and diethyl ether, respectively, and the resultant crude product was purified by TLC [developing solvent; ethyl acetate: n-hexane (9:1)] to obtain 3-methylene-17-aza-D-homoandrost-4-en-17a-one.

$^1$H-NMR (CDCl$_3$, δ): 1.05 (3H,s), 1.18 (3H,s), 3.1–3.5 (2H,m), 4.65 (2H,m), 5.57 (1H,br), 5.82 (1H,brs)

MS (m/z) : 299 (M$^+$), 284

Example 81

The procedures of Example 79 were repeated using D-homo-17-oxaandrost-4-ene-3,17a-dione and ethyltriphenylphosphonium bromide in place of D-homo-17-oxaandrost-4-en-3-one and methyltriphenylphosphonium bromide, respectively, and the resultant crude product was purified by TLC [developing solvent; n-hexane: ethyl acetate (3:1)] to obtain 3-ethylidene-D-homo-17-oxaandrost-4-en-17a-one.

$^1$H-NMR (CDCl$_3$,δ): 1.04 (3H,s), 1.24 (3H,s), 4.0–4.6 (2H,m), 5.0–5.5 (1H,m), 5.72 (brs), 6.09 (brs)

MS (m/z): 314 (M$^+$), 299, 285

Example 82

The procedures of Example 79 were repeated using D-homo-17-oxaandrost-4-ene-3,6,17a-trione in place of D-homo-17-oxaandrost-4-en-3-one, and the resultant crude product was purl fled by TLC [developing solvent; chloroform: acetone (19:1)] to obtain 3-methylene-D-homo-17-oxaandrost-4-ene-6,17a-dione.

$^1$H-NMR (CDCl$_3$, δ): 1.02 (3H,s), 1.26 (3H,s), 4.0–4.7 (2H,m), 5.22 (2H,m), 6.83 (1H,s)

MS (m/z) : 314 (M$^+$), 299

Example 83

The procedures of Example 74 were repeated using 10 mg of D-homo-17-oxaandrost-4-ene-3,6-dione and 20 mg of isobutyryl chloride in place of D-homo-17-oxaandrost-4-ene-3,6,17a-trione and acetyl chloride to obtain 10 mg of 6-isobutyryloxy-D-homo-17-oxaandrosta-4,6-dien-3-one.

$^1$H-NMR (CDCl$_3$,δ): 1.08 (3H,s), 1.20 (3H,s), 1.26 (6H, d,J=7Hz), 2.72 (1H,sep,J=7Hz), 3.01 (1H,d,J=10.5Hz), 3.2–3.5 (1H,m), 3.45 (1H,d,J=10.5Hz), 4.0–4.2 (1H,m), 5.79 (1H,s), 5.88 (1H,d,J=2Hz)

MS (m/z): 372 (M$^+$), 302, 274

Example 84

The procedures of Example 74 were repeated using 7 mg of D-homo-17-oxaandrost-4-ene-3,6-dione and 20 mg of benzoyl chloride in place of D-homo-17-oxaandrost-4-ene-3,6,17a-trione and acetyl chloride, respectively, to obtain 4 mg of 6-benzoyloxy-D-homo-17-oxaandrosta-4,6-dien-3-one.

$^1$H-NMR (CDCl$_3$, δ) : 1.10 (3H,s) 1.26 (3H,s), 3.03 (1H,d,J=10.5Hz), 3.2–3.5 (1H,m), 3.48 (1H,d,J=10.5Hz), 4.0–4.2 (1H,m), 5.88 (1H,s), 6.05 (1H,d,J=2Hz), 7.3–7.8 (3H,m), 8.0–8.2 (2H,m)

MS (m/z): 406 (M$^+$), 391,378, 284

Preparation example 1

A mixture of 18 mg of 16-oxaandrost-4-ene-3,17-dione, 57 μl of acetic acid, 5 μl of ethanedithiol and 5.31 mg of p-toluenesulfonic acid was stirred at room temperature for 2 hours. Water was added to the reaction mixture, the mixture was extracted with ethyl acetate, and the organic layer was washed with 5% aqueous sodium bicarbonate solution, water and saturated saline, and dried over magnesium sulfate. The solvent was distilled out, and the resultant crude product was purified by TLC [developing solvent; chloroform: acetone (19:1)] to obtain 15 mg of 3,3-ethylenedithio-16-oxaandrost-4-en-17-one.

$^1$H-NMR (CDCl$_3$,δ): 1.05 (3H,s), 1.12 (3H,s), 3.0–3.6 (4H,m), 3.8–4.4 (2H,m), 5.53 (1H,brs)

MS (m/z): 364 (M$^+$), 349, 336, 321,304

Preparation example 2

The procedures of Preparation example 1 were repeated using 9 mg of 6α,7α-difluoromethylene-16-oxaandrost-4-ene-3,17-dione in place of 16-oxaandrost-4-ene-3,17-dione, and the resultant etude product was purified by TLC [developing solvent; benzene: ethyl acetate (19:1)] to obtain 10 mg of 3,3-ethylenedithio-6α,7α-difluoromethylene-16-oxaandrost-4-en-17-one.

$^1$H-NMR (CDCl$_3$, δ): 0.98 (3H,s), 1.14 (3H,s), 3.2–3.5 (4H,m), 3.9–4.5 (2H,m), 5.81 (1H,brs)

Preparation example 3

The procedures of Preparation example 1 were repeated using 4 mg of 6β,7β-difluoromethylene-16-oxaandrost-4-ene-3,17-dione in place of 16-oxaandrost-4-ene-3,17-dione, and the resultant crude product was purified by TLC (developing solvent; chloroform) to obtain 2 mg of 3,3-ethylenedithio-6β,7β-difluoromethylene-16-oxaandrost-4-en-17-one.

$^1$H-NMR (CDCl$_3$, δ): 0.99 (3H,d,J=1.5Hz), 1.13 (3H,s), 3.1–3.6 (4H,m), 3.9–4.5 (2H,m), 5.75 (1H,s)

Preparation example 4

A mixture of 32 mg of 16-oxaandrost-4-ene-3,6,17-trione, 1.7 ml of acetic acid, 0.93 ml of 0.14 M ethanedithiol-acetic acid solution and 0.17 ml of boron trifluoride-ether complex was stirred at room temperature for 5 hours. The reaction mixture was poured into water and extracted with ethyl acetate, and the extract was washed with 5% aqueous sodium bicarbonate solution, water and saturated saline and dried over anhydrous magnesium sulfate. The solvent was distilled out, and the resultant crude product was purified by TLC [developing solvent; chloroform: acetone (40:1)] to obtain 24 mg of 3,3-ethylenedithio-16-oxaandrost-4-ene-6,17-dione.

$^1$H-NMR (CDCl$_3$, δ): 1.02 (3H,s), 1.14 (3H,s), 3.2–3.5 (4H,m), 3.8–4.4 (2H,m), 6.38 (1H,s)

MS (m/z): 378 (M$^+$), 363, 350, 335

Preparation example 5

30% aqueous hydrogen peroxide was added to a mixture of 19 mg of 16-oxaandrost-4-ene-3,17-dione, 37 µl of 10% sodium hydroxide-methanol solution and 0.67 ml of methanol under ice cooling and stirring, and the mixture was left to stand at 0° C. for 24 hours. Water was added to the reaction mixture, the mixture was acidified with 3.6% aqueous hydrochloric acid solution and extracted with ethyl acetate, and the extract was washed with saturated saline. The organic layer was dried over anhydrous magnesium sulfate and the solvent was distilled out to obtain 16 mg of 4ξ,5-epxoy-16-oxa-5ξ-androstane-3,17-dione.

Preparation example 6

A mixture of 55 mg of 16-oxaandrost-4-ene-3,17-dione, 77 µl of boron trifluoride-ether complex and 77 µl of ethanedithiol was subjected to reaction at room temperature for 15 minutes. Water was added to the reaction mixture, the mixture was extracted with ethyl acetate, and the organic layer was washed with 5% aqueous sodium bicarbonate solution, water and saturated saline and then dried over anhydrous magnesium sulfate. The solvent was distilled out, and the resultant crude product was purified by TLC [developing solvent; chloroform: acetone (19:1)] to obtain 69 mg of 3,3-ethylenedithio-16-azaandrost-4-en-17-one.

$^1$H-NMR (CDCl$_3$, δ): 1.04 (3H,s), 1.05 (3H,s), 2.9–3.5 (6H,m), 5.52 (1H,brs), 5.5–5.8 (1H,br)

MS (m/z): 363 (M$^+$), 348, 335

Preparation example 7

The procedures of Preparation example 5 were repeated using 30 mg of 16-azaandrost-4-ene-3,17-dione in place of 16-oxaandrost-4-ene-3,17-dione to obtain 31 mg of 4ξ,5-eopxy-16-aza-5Ξ-androstane-3,17-dione.

Preparation example 8

A mixture of 50 mg of 3β-hydroxy-16-azaandrost-5-en-17-one, 60 mg of m-chloroperbenzoic acid and 5 ml of chloroform was stirred at room temperature for 3 hours. The reaction mixture was washed with 5% aqueous sodium bicarbonate solution and water, and dried over anhydrous magnesium sulfate. The solvent was distilled out, and the resultant crude product was purified by TLC [developing solvent; chloroform: methanol (19:1)] to obtain 28 mg of 5,6α-epoxy-3β-hydroxy-16-aza-5ξ-androstan-17-one.

$^1$H-NMR (CDCl$_3$, δ): 0.96 (3H,s), 1.13 (3H,s), 2.93 (1H, d,J=4Hz), 3.0–3.3 (2H,m), 3.4–3.9 (1H,br)

MS (m/z): 305 (M$^+$), 290, 287, 272

Preparation example 9

A mixture of 200 mg of D-homo-17-oxaandrost-4-ene-3,17a-dione, 3.9 ml of methylene chloride, 0.13 ml of ethanedithiol and 0.13 ml of boron trifluoride-ether complex was stirred at room temperature for 2 hours. Water was added to the reaction mixture and the product was extracted with ethyl acetate. The extract was washed with 5% aqueous sodium bicarbonate solution and water and dried over anhydrous magnesium sulfate. The solvent was distilled out, and the resultant crude product was purified by TLC [developing solvent; chloroform: acetone (39:1)] to obtain 250 mg of 3,3-ethylenedithio-D-homo-17-oxaandrost-4-en-17a-one.

$^1$H-NMR (CDCl$_3$, δ): 1.02 (3H,s), 1.23 (3H,s), 3.0–3.7 (4H,m), 4.0–4.7 (2H,m), 5.51 (1H,s)

MS (m/z): 378 (M$^+$), 350, 318

Preparation example 10

The procedures of Preparation example 9 were repeated using 90 mg of 6α,7α-difluoromethylene-D-homo-17-oxaandrost-4-ene-3,17a-dione in place of D-homo-17-oxaandrost-4-ene-3,17a-dione to obtain 57 mg of 6α,7α-oxaandrost-4-ene-3,17a-dioneandrost-4-en-17a-one.

$^1$H-NMR (CDCl$_3$, δ): 0.95 (3H,s), 1.24 (3H,s), 3.0–3.7 (4H,m), 4.1–4.7 (2H,m), 5.82 (1H,s)

MS (m/z): 426 (M$^+$), 398, 366

Preparation example 11

The procedures of Preparation example 5 were repeated using 49 mg of D-homo-17-oxaandrost-4-ene-3,17a-dione in place of 16-oxaandrost-4-ene-3,17-dione to obtain 52 mg of 4ξ,5-epoxy-D-homo-17-oxa-5ξ-androstane-3,17a-dione.

Preparation example 12

A mixture of 100 mg of D-homo-17-oxaandrost-4-ene-3,6,17a-trione, 2 ml of methylene chloride, 0.03 ml of ethanedithiol and 0.05 ml of boron trifluoride-ether complex was stirred under ice cooling for 40 minutes. Water was added to the reaction mixture and the product was extracted with ethyl acetate. The extract was washed with 5% aqueous sodium bicarbonate solution and water and dried over anhydrous magnesium sulfate. The solvent was distilled out, and the resultant crude product was purified by TLC [developing solvent; chloroform: acetone (19:1)] to obtain 89 mg of 3,3-ethylenedithio-D-homo-17-oxaandrost-4-ene-6,17a-dione.

$^1$H-NMR (CDCl$_3$, δ): 0 98 (3H,s), 1 25 (3H,s), 3.1–3.6 (4H,m), 4.0–4.7 (2H,m), 6.40 (1H,s)

MS (m/z): 392 (M$^+$), 377, 349

Preparation example 13

The procedures of Preparation example 9 were repeated using 109 mg of 17-aza-D-homoandrost-4-ene-3,17a-dione in place of D-homo-17-oxaandrost-4-ene-3,17a-dione, and the resultant crude product was purified by TLC [developing solvent; chloroform: acetone (2:1)] to obtain 117 mg of 3,3-ethylenedithio-17-aza-D-homoandrost-4-en-17a-one.

$^1$H-NMR (CDCl$_3$, δ): 1.02 (3H,s), 1.18 (3H,s), 3.0–3.6 (6H,m), 5.51 (1H,s), 5.64 (1H,brs)

MS (m/z): 377 (M$^+$), 349, 317

Preparation example 14

The procedures of Preparation example 5 were repeated using 60 mg of 17-aza-D-homoandrost-4-ene-3,17a-dione in place of 16-oxaandrost-4-ene-3,17-dione to obtain 48 mg of 4ξ,5-eopxy-17-aza-D-homo-5ξ-androstane-3,17a-diode.

Preparation example 15

A mixture of 20.5 g of orthoperiodic acid and 100 ml of water was added to a mixture of 29.2 g of 3β,16β-dihydroxyandrost-5-en-17-one, and the mixture was stirred at room temperature for 20 minutes. Water was added to the reaction mixture, and the precipitated crystals were collected by filtration, washed with water and dried to obtain 22.2 g of 3β-hydroxy-16-oxo-16,17-secoandrost-5-en-17-oic acid.

$^1$H-NMR (CDCl$_3$,δ): 1.00 (3H,s), 1.17 (3H,s), 3.3–3.8 (1H,m), 5.33 (1H,brs), 9.70 (1H,s)

MS (m/z): 320 (M$^+$), 302, 287, 274, 257

Preparation example 16

A mixture of 4 g of 3β-hydroxy-16-oxo-16,17-secoandrost-5-en-17-oic acid and 30 ml of saturated hydrogen chloride-methanol solution was left to stand at room temperature for 1 hour. Water was added to the reaction mixture and the product was extracted with ethyl acetate. The extract was washed with 5% aqueous sodium bicarbonate solution and water and dried over anhydrous magnesium sulfate. The solvent was distilled out to obtain 3.7 g of methyl 3β-hydroxy-16-oxo-16,17-secoandrost-5-en- 17-oate.

$^1$H-NMR (CDCl$_3$,δ): 1.00 (3H,s), 1.15 (3H,s), 3.2–3.8 (1H,m), 3.65 (3H,s), 5.32 (1H,m), 9.69 (1H,brs)

Preparation example 17

A mixture of 200 mg of methyl 3β-hydroxy-16-oxo-16, 17-secoandrost-5-en-17-oate, 80 mg of methylamine hydrochloride, 0.3 ml of 30% methylamine-ethanol solution, 300 mg of sodium cyanoborohydride, 2 ml of tetrahydrofuran and 2 ml of methanol was stirred at room temperature for 18 hours. 6.8 ml of 4N hydrochloric acid was added to the reaction mixture, and the mixture was stirred at room temperature for 1 hour. Water was added to the reaction mixture and the product was extracted with chloroform. The extract was washed with 5% aqueous sodium bicarbonate solution and water, and dried over anhydrous magnesium sulfate. The solvent was distilled out, and the resultant crude product was purified by TLC [developing solvent; chloroform: acetone (4:1)] to obtain 43 mg of 3B-hydroxy-17-methyl-17-aza-D-homoandrost-5-en-17a-one.

$^1$H-NMR (CDCl$_3$, δ) : 1.00 (3H,s), 1.12 (3H,s), 2.88 (3H,s), 3.0–3.8 (3H,m), 5.34 (1H,m)

MS (m/z): 317 (M$^+$), 303, 29.9, 284

Preparation example 18

The procedures of Preparation example 9 were repeated using 68 mg of 7α-methyl-D-homo-17-oxaandrost-4-ene-3, 17a-dione in place of D-homo-17-oxaandrost-4-ene-3,17a-dione to obtain 41 mg of 3,3-ethylenedithio-7α-methyl-D-homo-17-oxaandrost-4-en-17a-one.

$^1$H-NMR (CDCl$_3$, δ): 0.75 (3H,d,J=6.8Hz), 1.03 (3H,s), 1.23 (3H,s), 3.0–3.5 (4H,m), 4.0–4.7 (2H,m), 5.50 (1H,brs)

MS (m/z): 392 (M$^+$), 364, 332, 221

Preparation example 19

A mixture of 204 mg of 6α,7α-difluoromethyleneandrost-4-en-17-one, 480 mg of cupric bromide and 7.7 ml of methanol was stirred for 70 minutes. The insoluble matters were removed by filtration and the filtrate was concentrated. The product was extracted with ethyl acetate, and the extract was washed with water and dried over anhydrous magnesium sulfate. The solvent was distilled out to obtain 250 mg of 16α-bromo-6α,7α-difluoromethyleneandrost-4-en-17-one.

$^1$H-NMR (CDCl$_3$, δ): 0.94 (3H,s), 0.97 (3H,s), 4.5 (1H, m), 5.64 (1H,m)

MS (m/z): 398 (M$^+$), 383, 347, 319

Preparation example 20

A mixture of 270 mg of 16α-bromo-6α,7α-difluoromethyleneandrost-4-en-17-one, 37 mg of sodium hydroxide, 3.5 ml of water and 10.5 ml of dimethylformamide was stirred at room temperature for 40 minutes. Diluted hydrochloric acid was added to the reaction mixture and the product was extracted with ethyl acetate. The extract was washed with 5% aqueous sodium bicarbonate solution and water, and dried over anhydrous magnesium sulfate. The solvent was distilled out to obtain 224 mg of 6α,7α-difluoromethylene-16α-hydroxyandrost-4-en-17-one.

$^1$H-NMR (CDCl$_3$, δ): 0.97 (3H,s), 1.00 (3H,s), 4.40 (1H,m), 5.64 (1H,m)

MS (m/z) : 336 (M$^+$)

Preparation example 21

The reaction of Preparation example 15 was repeated using 6α,7α-difluoromethylene-16α-hydroxyandrost-4-en-17-one in place of 3β,16α-dihydroxyandrost-5-en-17-one. Water was added to the reaction mixture and the product was extracted with chloroform. The extract was washed with saturated aqueous sodium thiosulfate and water, and dried over anhydrous magnesium sulfate. The solvent was distilled out to obtain 228 mg of 6α,7α-difluoromethylene-16-oxo-16,17-secoandrost-4-en-17-oic acid.

Preparation example 22

The procedures of Preparation example 16 were repeated using 228 mg of 6α,7α-difluoromethylene-16-oxo-16,17-secoandrost-4-en-17-oic acid in place of 3β-hydroxy-16-oxo-16,17-secoandrost-5-en-17-oic acid to obtain 200 mg of methyl 6α,7α-difluoromethylene-16-oxo-16,17-secoandrost-4-en-17-oate.

Preparation example 23

A mixture of 16.5 g of methyl 3β-hydroxy-15-(2'-indoxylidene)-16-nor-15,17-secoandrost-5-en -17-oate, 11.91 g of p-toluenesulfonyl chloride and 25 ml of pyridine was stirred at room temperature for 8 hours. The reaction mixture was poured in ice water and the product was extracted with ethyl acetate. The extract was washed with 3.6% hydrochloric acid, 5% aqueous sodium bicarbonate solution and saturated saline, and dried over hydrous magnesium sulfate. The solvent was distilled out to obtain 25.19 g of methyl 15-(2'- indoxylidene)-3β-(p-toluenesulfonyloxy)-16-nor-15,17-secoandrost -5-en-17oate.

¹H-NMR (CDCl₃, δ): 0 98 (3H,s), 1.24 (3H,s), 2.43 (3H,s), 3.56 (3H,s), 4.1–4.6 (1H,brm), 5.1–5.3 (1H,brd,J=5Hz), 5.72 (1H,d,J=11Hz), 6.8–7.0 (3H,m), 7.3–7.9 (6H,m)

MS (m/z) : 417 (M⁺—p-TsOH), 400, 358

Preparation example 24

A mixture of 25.19 g of methyl 15-(2'-indoxylidene)-3β-(p-toluenesulfonyloxy)-16-nor-15,17 -secoandrost-5-en-17-oate, 50.38 g of potassium acetate and 500 ml of methanol was refluxed for 4 hours. The reaction mixture was concentrated under reduced pressure, water was added, and the product was extracted with ethyl acetate. The extract was washed with water and saturated saline, and dried over anhydrous magnesium sulfate. The solvent was distilled out to obtain 18.66 g of methyl 15-(2'-indoxylidene)-6β-methoxy-3α,5-cyclo-16-nor-15, 17-seco-5α-androstan-17-oate.

¹H-NMR (CDCl₃,δ): 0.4–0.7 (2H,m), 1.04 (3H,s), 1.30 (3H,s), 3.27 (3H,s), 3.57 (3H,s), 5.85 (1H,d,J=11 Hz), 6.8–7.7 (5H,m)

MS (m/z): 449 (M⁺), 417, 402, 400

Preparation example 25

A mixture of 18.66 g of methyl 15-(2'-indoxylidene)-6β-methoxy-3ξ,5-cyclo-16-nor-15,17 -seco-5α-androstan-17-oate and 460 ml of methylene chloride was cooled to −78° C., and ozone was passed therethrough until the reaction mixture turned green. Nitrogen was passed through the reaction mixture, the resultant yellow mixture was added dropwise to a mixture of 18.66 g of zinc dust and 60 ml of acetic acid at 0° C., the mixture was stirred at the same temperature for 3 hours. The insoluble matters were removed from the reaction mixture by filtration, water and 72 g of potassium carbonate were added, and the mixture was stirred at room temperature for 10 minutes. The insoluble matters were removed from the reaction mixture by filtration, and the organic layer was separated and dried over anhydrous sodium sulfate. The solvent was distilled out, and the resultant crude product was purified by silica gel column chromatography (developing solvent; methylene chloride) to obtain 4.44 g of methyl 6β-methoxy-15-oxo-3α,5-cyclo-16-nor-15,17-seco-5α-androstan-17-oate.

¹H-NMR (CDCl₃,δ) :0.4–0.7 (2H,m), 1.05 (3H,s), 1.30 (3H,s), 3.32 (3H,s), 3.70 (3H,s), 9.73 (1H,d,J=3Hz)

MS (m/z): 334 (M⁺), 319, 316, 302

Preparation example 26

A mixture of 205 mg of methyl 6β-methoxy-15-oxo-3α,5-cyclo-16-nor-15,17-seco-5α -androstan-17-oate, 120 mg of lithium aluminum hydride and 5 ml of tetrahydrofuran was stirred at room temperature for 24 hours. The reaction mixture was poured in ice water, methylene chloride was added, and the insoluble matters were removed by filtration. The organic layer was separated and dried over anhydrous magnesium sulfate. The solvent was distilled out, and the resultant crude product was purified by TLC [developing solvent; chloroform: methanol (19:1)] to obtain 128 mg of 6β-methoxy-3α,5-cyclo-16-nor-15,17-seco-5α-androstane-15, 17-diol.

¹H-NMR (CDCl₃,δ): 0.4–0.7 (2H,m), 0.86 (3H,s), 1.01 (3H,s), 2.1–2.4 (1H,m), 2.7–2.9 (3H,brm), 3.1–3.8 (3H,m), 3.34 (3H,s)

MS (m/z): 308 (M⁺), 293, 390, 277, 276, 275

Preparation example 27

A mixture of 109 mg of 6β-methoxy-3α,5-cyclo-16-nor-15,17-seco-5α-androstane-15,17-diol, 76 mg of p-toluenesulfonyl chloride and 0.5 ml of pyridine was stirred at room temperature for 5 hours. Water was added to the reaction mixture and the product was extracted with ethyl acetate. The extract was washed with 3.6% hydrochloric acid, 5% aqueous sodium bicarbonate solution and saturated saline, and dried over anhydrous magnesium sulfate. The solvent was distilled out, and the resultant crude product was purified by TLC. (developing solvent; chloroform) to obtain 33 mg of 6β-methoxy-3α,5-cyclo-16-oxa-5α-androstane.

¹H NMR (CDCl₃,δ) : 0.4–0.7 (2H,m), 0.98 (3H,s), 1.06 (3H,s), 2.76 (1H,t,J=3Hz), 3.3–4.0 (4H,m), 3.32 (3H,s)

MS (m/z): 290 (M⁺), 275, 258, 243, 235

Preparation example 28

A mixture of 27 mg of 6β-methoxy-3α,5-cyclo-16-oxa-5α-androstane, 0.5 ml of dioxane and 82 μl of aqueous sulfuric acid solution (1 drop/5 ml) was refluxed for 1 hour. Water was added to the reaction mixture and the product was extracted with ethyl acetate. The extract was washed with 5% aqueous sodium bicarbonate solution and saturated saline, and dried over anhydrous magnesium sulfate. The solvent was distilled out, and the resultant crude product was purified by TLC [developing solvent; chloroform: acetone (19:1)] to obtain 23 mg of 16-oxaandrost-5-en-3β-ol.

¹H-NMR (CDCl₃, δ): 0.94 (3H,s), 1.04 (3H,s), 3.3–4.0 (4H,m), 5.2–5.4 (1H,br)

MS (m/z) : 276 (M⁺), 261, 258, 243

Preparation example 29

A mixture of 350 mg of 16,17-secoandrost-5-ene-3β,16,17-triol, 630 mg of p-toluenesulfonyl chloride and 9 ml of pyridine was stirred at room temperature for 20 hours. Water was added to the reaction mixture and the product was extracted with ethyl acetate. The extract was washed with 3.6% hydrochloric acid, 5% aqueous sodium bicarbonate solution and saturated saline, and dried over anhydrous magnesium sulfate. The solvent was distilled out to obtain a mixture of D-homo-17-oxaandrost-5-en-3β-ol and D-homo-17-oxaandrost-5-en-3β-yl p-toluenesulfonate. A mixture of this mixture, 1.3 g of potassium acetate and 14 ml of methanol was refluxed for 3 hours. Water was added to the reaction mixture and the product was extracted with diethyl ether. The extract was washed with 5% aqueous sodium bicarbonate solution and saturated saline, and dried over anhydrous sodium sulfate. The solvent was distilled out to obtain a mixture of D-homo-17-oxaandrost-5-en-3β-ol and 6β-methoxy-3α,5-cyclo-D-homo-17-oxa-5α-androstane. A mixture of this mixture, 7.3 ml of dioxane, 1.2 ml of water and 1 drop of concentrated sulfuric acid was refluxed for 1 hour. Water was added to the reaction mixture and the product was extracted with ethyl acetate. The extract was washed with 5% aqueous sodium bicarbonate solution and saturated saline, and dried over anhydrous magnesium sulfate. The solvent was distilled out to obtain 330 mg of D-homo-17-oxaandrost-5-en-3β-ol.

¹H-NMR (CDCl₃, δ): 1.01 (6H,s), 2.98,3.38 (2H,ABq,J=11Hz), 3.2–3.8 (2H,m), 4.10 (1H,m), 5.35 (1H,m)

MS (m/z): 290 (M⁺), 275, 272, 257

Preparation example 30

A mixture of 220 mg of 3β-hydroxy-D-homo-17-oxaandrost-5-en-17a-one, 320 mg of tri-tert-butoxyaluminolithium hydride and 6 ml of tetrahydrofuran was stirred at 0° C. for 20 minutes. Water and 5% hydrochloric acid were added to the reaction mixture, and the product was extracted with ethyl acetate. The extract was washed with 5% aqueous sodium bicarbonate solution and saturated saline, and dried over anhydrous magnesium sulfate. The solvent was distilled out to obtain D-homo-17-oxaandrost-5-ene-3α,17aξ-diol.

Preparation example 31

A mixture of 90 mg of D-homo-17-oxaandrost-5-ene-3β,17aξ-diol, 0.08 ml of triethylsilane, 0.05 ml of boron trifluoride-diethyl ether complex and 2.5 ml of methylene chloride was stirred under a nitrogen stream at 0° C. for 10 minutes. 5% aqueous sodium bicarbonate solution was added to the reaction mixture and the mixture was stirred at room temperature for 10 minutes. The product was extracted with ethyl acetate, and the extract was washed with 5% aqueous sodium bicarbonate solution and saturated saline, and dried over anhydrous magnesium sulfate. The solvent was distilled out to obtain 80 mg of D-homo-17-oxaandrost-5-en-3β-ol.

Preparation example 32

A mixture of 400 mg of D-homo-17-oxaandrost-4-en-3-one, 10% aqueous sodium hydroxide solution, 30% aqueous hydrogen peroxide and 30 ml of methanol was stirred at 0° C. for 8 hours. Water was added to the reaction mixture and the product was extracted with ethyl acetate. The extract was washed with saturated saline, and dried over anhydrous magnesium sulfate. The solvent was distilled out to obtain 403 mg of 4ξ,5-epoxy-D-homo-17-oxa-5ξ-androstan-3-one.

Preparation example 33

A mixture of 30 mg of D-homo-17-oxaandrost-4-en-3-one, 0.02 ml of ethanedithiol, 0.02 ml of boron trifluoride-diethyl ether complex and 6 ml of methylene chloride was stirred at room temperature for 6 hours. 5% aqueous sodium bicarbonate solution was added to the reaction mixture and the product was extracted with ethyl acetate. The extract was washed with saturated saline and dried over anhydrous magnesium sulfate. The solvent was distilled out, and the resultant crude product was purified by TLC [developing solvent; chloroform: acetone (19:1)] to obtain 35 mg 3,3-ethylenedithio-D-homo-17-oxaandrost-4-ene.

$^1$H-NMR (CDCl$_3$ δ): 0.99 (3H,s), 1.02 (3H,s), 2.96 (1H,d,J=11Hz), 3.1–3.6 (6H,m), 4.0 (1H,m), 5.49 (1H,s)

MS (m/z): 364 (M$^+$), 336, 304, 271

Preparation example 34

The procedures of Preparation example 33 were repeated using 62 mg of 7α-methyl-D-homo-17-oxaandrost-4-en-3-one in place of D-homo-17-oxaandrost-4-en-3-one to obtain 77 mg of 3,3-ethylenedithio-7α-methyl-D-homo-17-oxaandrost-4-ene.

$^1$H-NMR (CDCl$_3$ δ): 0.72 (3H,d,J=7Hz), 0.99 (3H,s), 1.02 (3H,s), 2.96 (1H,d,J=11Hz), 3.1–3.6 (6H,m), 4.0 (1H,m), 5.47 (1H,s)

MS (m/z): 378 (M$^+$), 350, 318, 285

Preparation example 35

The procedures of Preparation example 33 were repeated using 50 mg of 6α,7α-difluoromethylene-D-homo-17-oxaandrost-4-en-3-one in place of D-homo-17-oxaandrost-4-en-3-one to obtain 53 mg of 6α,7α-difluoromethylene-3,3-ethylenedithio-D-homo-17-oxaandrost-4-ene.

$^1$H-NMR (CDCl$_3$ δ): 0.94 (3H,s), 1.01 (3H,s), 2.99 (1H,d,J=11Hz), 3.1–3.6 (6H,m), 4.05 (1H,m), 5.78 (1H,brs)

MS (m/z): 412 (M$^+$), 397, 384, 352

Preparation example 36

A mixture of 5.1 g of 6β-methoxy-3α,5-cyclo-5α-androstan-17-one, 15 g of m-chloroperbenzoic acid and 100 ml of chloroform was stirred at room temperature for 20 hours. Water was added to the reaction mixture and the product was extracted with chloroform. The extract was washed with 5% aqueous sodium thiosulfate solution, 5% aqueous sodium bicarbonate solution and saturated saline, and dried over anhydrous magnesium sulfate. The solvent was distilled out, and the resultant crude product was purified by silica gel column chromatography (eluent; chloroform) to obtain 2.9 g of 6β-methoxy-3α,5-cyclo-D-homo-17a-oxa-5α-androstan-17-one.

$^1$H-NMR (CDCl$_3$ , δ) : 1.01 (3H,s), 1.35 (3H,s), 2.83 (1H,t,J=3Hz), 3.33 (3H,s)

MS (m/z): 318 (M$^+$), 303, 286, 263

Preparation example 37

A mixture of 2 g of 6β-methoxy-3α,5-cyclo-D-homo-17a-oxa-5α-androstan-17-one, 100 ml of toluene and 8 ml of 25% diisobutylaluminum hydride-toluene solution was stirred at −78° C. for 2 hours. Water and diluted hydrochloric acid was added to the reaction mixture, and the product was extracted with chloroform. The extract was washed with saturated saline and dried over anhydrous magnesium sulfate. The solvent was distilled out to obtain 1.9 g 6β-methoxy-3α,5-cyclo-D-homo-17a-oxa-5α-androstan-17α-ol.

Preparation example 38

2.1 g of mercury (II) oxide and 2.5 g of iodine were added to a mixture of 1.9 g of 6β-methoxy-3α,5-cyclo-D-homo-17a-oxa-5α-androstan-17α-ol, 475 ml of benzene and 12 ml of pyridine, and the mixture was irradiated with a 500 W tungsten lamp for 2 hours under a nitrogen stream. The insoluble matters were removed by filtration, and the organic layer was washed with 5% aqueous sodium thiosulfate solution, 5% hydrochloric acid, 5% aqueous sodium bicarbonate solution and saturated saline and dried over anhydrous magnesium sulfate. The solvent was distilled out to obtain 2 g of 16-iodo-6β-methoxy-3α,5-cyclo-17-nor-13,16-seco-5α-androstan-13α-yl formate.

Preparation example 39

A mixture of 16-iodo-6β-methoxy-3α,5-cyclo-17-nor-13,16-seco-5α-androstan-13α-yl formate, sodium borohydride and tetrahydrofuran was refluxed for 17 hours. 5% hydrochloric acid was added to the reaction mixture and the product was extracted with ethyl acetate. The extract was washed with 5% aqueous sodium bicarbonate solution and saturated saline and dried over anhydrous magnesium sulfate. The solvent was distilled out to obtain 6β-methoxy-3α,5-cyclo-17-oxa-5α-androstane.

Preparation example 40

The procedures of Preparation example 28 were repeated using 6β-methoxy-3α,5-cyclo-17-oxa-5α-androstane in place of 6β-methoxy-3α,5-cyclo-16-oxa-5α-androstane to obtain 17-oxaandrost-5-en-3β-ol.

$^1$H-NMR (CDCl$_3$,δ): 0.98 (3H,s), 1.07 (3H,s), 3.3–3.8 (1H,m), 3.7–4.1 (2H,m), 5.36 (1H,m)

MS (m/z) : 276 (M$^+$), 261

Preparation example 41

The procedures of Preparation example 32 were repeated using 46 mg of 17-oxaandrost-4-en-3-one in place of D-homo-17-oxaandrost-4-en-3-one to obtain 48 mg of 4ξ,5-epoxy-17-oxa-5ξ-androstan-3-one.

Preparation example 42

The procedures of Preparation example 26 were repeated using 6β-methoxy-3α,5-cyclo-D-homo-17a-oxa-5α-androstan-17-one in place of methyl 6β-methoxy-15-oxo-3α,5-cyclo-16-nor-15,17-seco-5α-androstan-17-oate to obtain 6β-methoxy-3α,5-cyclo-13,17-seco-5α-androstane-13α,17-diol.

$^1$H-NMR (CDCl$_3$, δ): 0.98 (3H,s), 1.16 (3H,s), 2.81 (1H,t,J=3Hz), 3.33 (3H,s), 3.5–3.9 (2H,m)

Preparation example 43

The procedures of Preparation example 27 were repeated using 6β-methoxy-3α,5-cyclo-13,17-seco-5α-androstane-13α,17-diol in place of 6β-methoxy-3α,5-cyclo-16-nor-15,17-seco-5α-androstane-15,17-diol to obtain 6β-methoxy-3α,5-cyclo-D-homo-17a-oxa-5α-androstane.

$^1$H-NMR (CDCl$_3$,δ): 1.00 (3H,s), 1.19 (3H,s), 2.80 (1H, t,J=3Hz), 3.32 (3H,s), 3.5–3.8 (2H,m)

Preparation example 44

The procedures of Preparation example 28 were repeated using 6β-methoxy-3α,5-cyclo-D-homo-17a-oxa-5α-androstane in place of 6β-methoxy-3α,5-cyclo-16-oxa-5α-androstane to obtain D-homo-17a-oxaandrost-5-en-3β-ol.

$^1$H-NMR (CDCl$_3$, δ) : 0.97 (3H,s), 1.16 (3H,s), 3.3–3.9 (3H,m), 5.35 (1H,m)

Preparation example 45

The procedures of Preparation example 30 were repeated using 100 mg of D-homo-17-oxaandrost-4-ene-3,17a-dione in place of 3β-hydroxy-D-homo-17-oxaandrost-5-en-17a-ol to obtain 100 mg of 17aξ-hydroxy-D-homo-17-oxaandrost-4-en-3-one.

An example of preparation of a pharmaceutical containing a compound of this invention is shown below.

Preparation example A: tablet

|  | mg/table |
|---|---|
| Active ingredient | 100 |
| starch | 20 |
| Lactose | 105.5 |
| Carboxymethylcellulose calcium | 20 |
| Talc | 3 |
| Magnesium stearate | 1.5 |
|  | 250 mg |

The active ingredient is pulverized to a particle size of 70 μ or less, the starch, the lactose and the carboxymethylcellulose calcium are added thereto, and the mixture is sufficiently mixed. 10% of starch paste is added to the above mixed fine particles and granules are prepared. The granules are graded to a particle size after drying of about 1,000 μ, the talc and the magnesium stearate are added thereto, and the mixture is tableted. Industrial Applicability The compounds of this invention represented by the formula (I) have an aromatase inhibition action and are useful for prophylaxis or treatment of diseases caused by excess of estrogens, for example, breast cancer, uteric cancer, prostatic hypertrophy, etc.

We claim:

1. Steroid derivatives represented by the formula

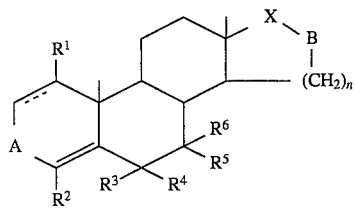

wherein $R^1$ denotes a hydrogen atom or a lower alkyl group;

$R^2$ denotes a hydrogen atom, a halogen atom, or a hydroxyl, mercapto or amino group which may optionally be acylated or lower alkylated;

$R^3$, $R^4$, $R^5$, and $R^6$ denote one of the following (a) to (d):

(a) $R^3$ and $R^5$ each denote a hydrogen atom, and $R^4$ and $R^6$ each denote a hydrogen atom, a halogen atom or a lower alkyl group, (b) $R^3$ and $R^6$ each denote a hydrogen atom, and $R^4$ and $R^5$ combine to denote a single bond, a methylene group or a dihalomethylene group, (c) $R^3$ and $R^4$ combine to denote an oxo group or a methylene group, and $R^5$ and $R^6$ each denote a hydrogen atom, (d) $R^3$ denotes an acyloxy group, $R^4$ and $R^5$ combine to denote a single bond, and $R^6$ denotes a hydrogen atom;

A denotes C=O, CH$_2$, C=CH$_2$ or C=CH-lower alkyl;

B denotes O denotes C=O or CH$_2$;

n denotes 2; and the broken line between the 1- and 2-positions of the steroid skeleton means that a double bond may optionally exist there.

2. The steroid derivatives according to claim 1 wherein $R^2$ denotes a hydrogen atom, a halogen atom, a hydroxyl group or an amino group; and either $R^3$, $R^4$ and $R^5$ each denote a hydrogen atom and $R^6$ denotes a hydrogen atom or a lower alkyl group, or $R^3$ and $R^6$ each denote a hydrogen atom and $R^4$ and $R^5$ combine to denote a single bond, a methylene group or a dihalomethylene group, or $R^3$ and $R^4$ combine to demote an oxo group or a methylene group and $R^5$ and $R^6$ each denote a hydrogen atom.

3. An aromatase inhibitor containing a compound according to claim 1.

4. A pharmaceutical composition comprising a compound according to claim 1 and a pharmaceutically acceptable adjuvant.

5. The composition according to claim 4 for prophylaxis or treatment of diseases caused by excess of estrogens.

* * * * *